US007564990B2

(12) United States Patent
Kern et al.

(10) Patent No.: US 7,564,990 B2
(45) Date of Patent: Jul. 21, 2009

(54) IMAGING SYSTEM AND METHOD FOR PHYSICAL FEATURE ANALYSIS

(75) Inventors: Dale G. Kern, Hyde Park, UT (US);
Kurt L. Jensen, Spanish Fork, UT (US);
Joseph H. Labrum, Orem, UT (US);
Mark W. Lund, Orem, UT (US); Jed G. Morley, Orem, UT (US)

(73) Assignee: Nu Skin International, Inc., Provo, UT (US)

( * ) Notice: Subject to any disclaimer, the term of this patent is extended or adjusted under 35 U.S.C. 154(b) by 449 days.

(21) Appl. No.: 11/206,671

(22) Filed: Aug. 18, 2005

(65) Prior Publication Data

US 2007/0040907 A1 Feb. 22, 2007

(51) Int. Cl.
*G06K 9/00* (2006.01)
*A01K 43/00* (2006.01)
(52) U.S. Cl. .......................... 382/100; 382/274; 356/66
(58) Field of Classification Search ................. 382/100, 382/106, 108, 118, 162, 168, 219, 181–195, 382/224, 232, 260, 274, 276, 305, 313–321, 382/128, 254; 235/454; 600/309; 356/73, 356/66; 359/810
See application file for complete search history.

(56) References Cited

U.S. PATENT DOCUMENTS

| | | | | |
|---|---|---|---|---|
| 5,442,489 A | * | 8/1995 | Yamamoto et al. | 359/810 |
| 5,885,211 A | * | 3/1999 | Eppstein et al. | 600/309 |
| 6,118,521 A | * | 9/2000 | Jung et al. | 356/73 |
| 6,571,003 B1 | * | 5/2003 | Hillebrand et al. | 382/118 |
| 7,240,839 B2 | * | 7/2007 | Jung et al. | 235/454 |
| 2004/0218810 A1 | * | 11/2004 | Momma | 382/162 |

OTHER PUBLICATIONS http://www.dermlite.com; Dermlite® multispectral, pp. 1-4 (2006).

(Continued)

*Primary Examiner*—Seyed Azarian
(74) *Attorney, Agent, or Firm*—Stuart R. Hemphill; Dorsey & Whitney LLP

(57) ABSTRACT

A system for capturing and analyzing images of body features to identify treatments has a base unit with a processor and a display and an image management software component for presenting on the display a user interface to prompt a user to capture images in preselected locations on a body and to receive captured image data. The system has at least two light sources under control of the user interface that provide light following first and second light paths from the respective light sources to the plane of an imaging station, each light path having a significant portion of its light on the plane of the imaging station at a grazing angle of about ten to about thirty degrees. The first and second light paths when projected onto the plane of the imaging station intersect at an angle of at least sixty degrees. An image sensor receives light from the light sources that is reflected from the surface of a body feature located at the imaging station and produces pixel image data representing the body feature. A rating software component receives the pixel image data from the image sensor and is configured to mimic the judgment of a dermatologist to provide a rating vector representing the condition of three or more attributes of the body feature represented by the pixel image data.

43 Claims, 28 Drawing Sheets

OTHER PUBLICATIONS http;//homepages.inf.ed.ac.uk/rbf/HIPR2/gsmooth.htm; Gaussian Smoothing, pp. 1-8 (2006).

http://www.ph.tn.tudelft.nl/Courses.FIP/noframes/fip-Smoothin.html;Image Processing Fundamentals - Smoothing Operations; pp. 1-6 (2006).

http:www.ph.tn.tudelft.nl/Courses.FIP/noframes/fip-Derivati.html: Image Processing Fundamentals - Derivative-based Operations; pp. 1-7 (2006).

http://www.websupergoo.com/helpie/source/2-effects/laplacian.htm; Laplacian; pp. 1-3 (2006).

http;//www.cambridgeincolour.com/tutorials/histograms1.htm: Tutorials: Image Histograms - Part 1; pp. 1-5.

http;//www.deming.eng.Clemson.edu/pub/tutorials.qctools.histm.htm; Histograms; pp. 1-9 (2006).

http://luminous-landscape.com/tutorials/understanding-series/understanding-histograms.shtml; The Luminous Landscape; pp. 1-11 (2006).

http://www.pages.Drexel.edu/~weg22/hist_tresh_cent.html; Histogram, Thresholding and Image Centroid Tutorial; pp. 1-6 (2006).

http:/www.incx/nec.cojp/imap-vision/library/wouter/avef5gaus.html; Gaussian 5 x 5 average filter; pp. 1-2 (2006).

http://www.moritex.co.jp/, "Fast, Accurate Skin Analysis Moritex Leads The Way - What Our Products can do for your skin", *Cosmetic Arts General Catalog*, Moritex Corporation, pp. 1-35 (2006).

http://www.nuskin.com/corp/product/regopt.shtml (2006).

http://www.nuskin.com/corp/library/pdf/pip-regoptimizer.pdf Nu Skin Product Information, 2 pgs., 2004.

http://www.nuskin.com/corp/library/pdf/regoptimizer-userguide.pdf (20060.

PCT International Search Report (2006).

http://www.dai.ed.ac.uk/HIPR2/log.htm (2003).

http://www.opengl.org/resources/codes/samples/advanced/advanced97/notes/nodel171.html#Section. . . (2006).

\* cited by examiner

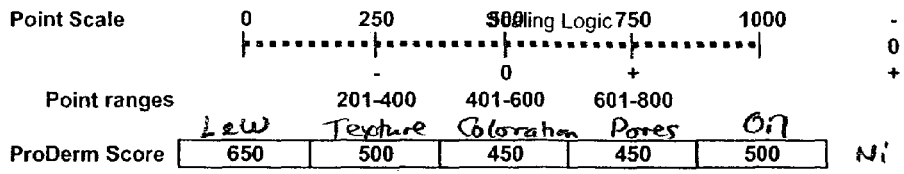

| Point Scale | 0 | 250 | S8ling Logic 750 | 1000 | |
|---|---|---|---|---|---|
| | ⊢••••••••⊢••••••••⊢••••••••⊢••••••••⊣ | | | | 0 |
| | | - | 0 | + | + |
| Point ranges | | 201-400 | 401-600 | 601-800 | |
| | L&W | Texture | Coloration | Pores | Oil |
| ProDerm Score | 650 | 500 | 450 | 450 | 500 | Ni

| Scoring Weighting | | | | | | |
|---|---|---|---|---|---|---|
| | L & W | Texture | Coloration | Pores | Oil | Total |
| 180 | 100 | 100 | - | - | - | 200 |
| TPW | - | 100 | 100 | 20 | - | 220 |
| CA | - | 90 | 40 | 40 | 30 | 200 |
| Nutri. C/O | - | 50 | - | 20 | 90 | 160 |
| Nutri. N/D | - | 90 | - | 50 | - | 140 |

| Scoring Weighting as a % (Wip) | | | | | | |
|---|---|---|---|---|---|---|
| | L & W | Texture | Coloration | Pores | Oil | Total |
| 180 | 50% | 50% | 0% | 0% | 0% | 100% |
| TPW | 0% | 45% | 45% | 9% | 0% | 100% |
| CA | 0% | 45% | 20% | 20% | 15% | 100% |
| Nutri. C/O | 0% | 31% | 0% | 13% | 56% | 100% |
| Nutri. N/D | 0% | 64% | 0% | 36% | 0% | 100% |

| Scoring (ANip) | | | | | | Final Score |
|---|---|---|---|---|---|---|
| | L & W | Texture | Coloration | Pores | Oil | |
| 180 | 325 | 250 | - | - | - | 575 |
| TPW | - | 227 | 205 | 41 | - | 473 |
| CA | - | 225 | 90 | 90 | 75 | 480 |
| Nutri. C/O | - | 156 | - | 56 | 281 | 494 |
| Nutri. N/D | - | 321 | - | 161 | - | 482 |

} TANip

Fig. 18

| | Prod. Recg. | L & W | Text. | Color. | Pores | Oil | Additional Product? |
|---|---|---|---|---|---|---|---|
| 1 | Nutricentials N/D | + | + | + | + | + | Polish Peel/Revealing Gel |
| 2 | Nutricentials C/O | + | + | + | + | 0 | GMM |
| 3 | Nutricentials C/O | + | + | + | + | - | GMM |
| 4 | Nutricentials N/D | + | + | + | 0 | + | Polish Peel/Revealing Gel |
| 5 | Nutricentials C/O | + | + | + | 0 | 0 | Polish Peel/Revealing Gel |
| 6 | Nutricentials C/O | + | + | + | 0 | - | GMM |
| 7 | Nutricentials C/O | + | + | + | - | + | Polish Peel/Revealing Gel |
| 8 | Nutricentials C/O | + | + | + | - | 0 | Polish Peel/Revealing Gel |
| 9 | Nutricentials C/O | + | + | + | - | - | GMM |
| 10 | TPW | + | - | 0 | + | + | |
| 11 | TPW | + | - | 0 | + | 0 | |
| 12 | TPW | + | - | 0 | + | - | |
| 13 | TPW | + | - | 0 | 0 | + | |
| 14 | TPW | + | - | 0 | 0 | 0 | |
| 15 | TPW | + | - | 0 | 0 | - | |
| 16 | TPW | + | - | 0 | - | + | |
| 17 | TPW | + | - | 0 | - | 0 | |
| 18 | TPW | + | - | 0 | - | - | |
| 19 | TPW | + | - | - | + | + | |
| 20 | TPW | + | - | - | + | 0 | |
| 21 | TPW | + | - | - | + | - | |
| 22 | TPW | + | - | - | 0 | + | |
| 23 | TPW | + | - | - | 0 | 0 | |
| 24 | TPW | + | - | - | 0 | - | |
| 25 | TPW | + | - | - | - | + | |
| 26 | TPW | + | - | - | - | 0 | |
| 27 | TPW | + | - | - | - | - | |
| 28 | Nutricentials N/D | + | 0 | + | + | + | Polish Peel/Revealing Gel |
| 29 | Nutricentials C/O | + | 0 | + | + | 0 | Polish Peel/Revealing Gel |
| 30 | Nutricentials C/O | + | 0 | + | + | - | GMM |
| 31 | Nutricentials N/D | + | 0 | + | 0 | + | Polish Peel/Revealing Gel |
| 32 | Nutricentials C/O | + | 0 | + | 0 | 0 | Polish Peel/Revealing Gel |
| 33 | Nutricentials C/O | + | 0 | + | 0 | - | GMM |
| 34 | Nutricentials C/O | + | 0 | + | - | + | Polish Peel/Revealing Gel |
| 35 | Nutricentials C/O | + | 0 | + | - | 0 | Polish Peel/Revealing Gel |
| 36 | Nutricentials C/O | + | 0 | + | - | - | Polish Peel/Revealing Gel |
| 37 | TPW | + | 0 | 0 | + | + | |
| 38 | TPW | + | 0 | 0 | + | 0 | |
| 39 | TPW | + | 0 | 0 | + | - | |
| 40 | TPW | + | 0 | 0 | 0 | + | |
| 41 | TPW | + | 0 | 0 | 0 | 0 | |
| 42 | TPW | + | 0 | 0 | 0 | - | |
| 43 | TPW | + | 0 | 0 | - | + | |
| 44 | TPW | + | 0 | 0 | - | 0 | |
| 45 | TPW | + | 0 | 0 | - | - | |
| 46 | TPW | + | 0 | - | + | + | |
| 47 | TPW | + | 0 | - | + | 0 | |
| 48 | TPW | + | 0 | - | + | - | |
| 49 | TPW | + | 0 | - | 0 | + | |
| 50 | TPW | + | 0 | - | 0 | 0 | |
| 51 | TPW | + | 0 | - | 0 | - | |
| 52 | TPW | + | 0 | - | - | + | |

*Figure 19a*

| | | | | | | | |
|---|---|---|---|---|---|---|---|
| 53 | TPW | + | 0 | - | - | 0 | |
| 54 | TPW | + | 0 | - | - | - | |
| 55 | 180 | + | - | + | + | + | |
| 56 | 180 | + | - | + | + | 0 | |
| 57 | 180 | + | - | + | + | - | |
| 58 | 180 | + | - | + | 0 | + | |
| 59 | 180 | + | - | + | 0 | 0 | |
| 60 | 180 | + | - | + | 0 | - | |
| 61 | 180 | + | - | + | - | + | |
| 62 | 180 | + | - | + | - | 0 | |
| 63 | 180 | + | - | + | - | - | |
| 64 | TPW | + | - | 0 | + | + | |
| 65 | TPW | + | - | 0 | + | 0 | |
| 66 | TPW | + | - | 0 | + | - | |
| 67 | TPW | + | - | 0 | 0 | + | |
| 68 | TPW | + | - | 0 | 0 | 0 | |
| 69 | TPW | + | - | 0 | 0 | - | |
| 70 | TPW | + | - | 0 | - | + | |
| 71 | TPW | + | - | 0 | - | 0 | |
| 72 | TPW | + | - | 0 | - | - | |
| 73 | TPW | + | - | - | + | + | |
| 74 | TPW | + | - | - | + | 0 | |
| 75 | TPW | + | - | - | + | - | |
| 76 | TPW | + | - | - | 0 | + | |
| 77 | TPW | + | - | - | 0 | 0 | |
| 78 | TPW | + | - | - | 0 | - | |
| 84 | TPW | + | - | - | - | + | |
| 85 | TPW | + | - | - | - | 0 | |
| 86 | TPW | + | - | - | - | - | |
| 87 | 180 if over 30, Nutricentials | 0 | + | + | + | + | |
| 88 | 180 if over 30, Nutricentials | 0 | + | + | + | 0 | GMM |
| 89 | 180 if over 30, Nutricentials | 0 | + | + | + | - | GMM |
| 90 | 180 if over 30, Nutricentials | 0 | + | + | 0 | + | Polishing Peel/Revealing Gel |
| 91 | 180 if over 30, Nutricentials | 0 | + | + | 0 | 0 | Polishing Peel/Revealing Gel |
| 92 | 180 if over 30, Nutricentials | 0 | + | + | 0 | - | GMM |
| 93 | 180 if over 30, Nutricentials | 0 | + | + | - | + | Polishing Peel/Revealing Gel |
| 94 | 180 if over 30, Nutricentials | 0 | + | + | - | 0 | Polishing Peel/Revealing Gel |
| 95 | 180 if over 30, Nutricentials | 0 | + | + | - | - | Polishing Peel/Revealing Gel |
| 96 | 180 if over 30, Nutricentials | 0 | + | + | + | + | |
| 97 | 180 if over 30, Nutricentials | 0 | + | + | + | 0 | GMM |
| 98 | 180 if over 30, Nutricentials | 0 | + | + | + | - | GMM |
| 99 | 180 if over 30, Nutricentials | 0 | + | + | 0 | + | |

*Figure 19b*

| | | | | | | | |
|---|---|---|---|---|---|---|---|
| 100 | 180 if over 30, Nutricentials | 0 | + | 0 | 0 | 0 | Polishing Peel/Revealing Gel |
| 101 | 180 if over 30, Nutricentials | 0 | + | 0 | 0 | - | GMM |
| 102 | 180 if over 30, Nutricentials | 0 | + | 0 | - | + | Polishing Peel/Revealing Gel |
| 83 | 180 if over 30, Nutricentials | 0 | + | 0 | - | 0 | Polishing Peel/Revealing Gel |
| 103 | 180 if over 30, Nutricentials | 0 | + | 0 | - | - | Polishing Peel/Revealing Gel |
| 104 | TPW | 0 | + | - | + | + | |
| 105 | TPW | 0 | + | - | + | 0 | |
| 106 | TPW | 0 | + | - | + | - | |
| 107 | TPW | 0 | + | - | 0 | + | |
| 108 | TPW | 0 | + | - | 0 | 0 | |
| 109 | TPW | 0 | + | - | 0 | - | |
| 110 | TPW | 0 | + | - | - | + | |
| 80 | TPW | 0 | + | - | - | 0 | |
| 111 | TPW | 0 | + | - | - | - | |
| 112 | 180 | 0 | 0 | + | + | + | |
| 113 | 180 | 0 | 0 | + | + | 0 | |
| 114 | 180 | 0 | 0 | + | + | - | |
| 115 | 180 | 0 | 0 | + | 0 | + | |
| 116 | 180 | 0 | 0 | + | 0 | 0 | |
| 117 | 180 | 0 | 0 | + | 0 | - | |
| 118 | 180 | 0 | 0 | + | - | + | |
| 119 | 180 | 0 | 0 | + | - | 0 | |
| 120 | 180 | 0 | 0 | + | - | - | |
| 121 | 180 | 0 | 0 | + | + | + | |
| 122 | 180 | 0 | 0 | 0 | + | 0 | |
| 123 | 180 | 0 | 0 | 0 | + | - | |
| 124 | 180 | 0 | 0 | 0 | 0 | + | |
| 125 | 180 | 0 | 0 | 0 | 0 | 0 | |
| 82 | 180 | 0 | 0 | 0 | 0 | - | |
| 126 | 180 | 0 | 0 | 0 | - | + | |
| 127 | 180 | 0 | 0 | 0 | - | 0 | |
| 128 | 180 | 0 | 0 | - | - | - | |
| 129 | TPW | 0 | 0 | - | + | + | |
| 130 | TPW | 0 | 0 | - | + | 0 | |
| 131 | TPW | 0 | 0 | - | + | - | |
| 132 | TPW | 0 | 0 | - | 0 | + | |
| 133 | TPW | 0 | 0 | - | 0 | 0 | |
| 134 | TPW | 0 | 0 | - | 0 | - | |
| 135 | TPW | 0 | 0 | - | - | + | |
| 136 | TPW | 0 | 0 | - | - | 0 | |
| 137 | TPW | 0 | 0 | + | - | - | |
| 138 | 180 | 0 | 0 | + | + | + | |
| 139 | 180 | 0 | - | + | + | 0 | |
| 140 | 180 | 0 | - | + | + | - | |
| 141 | 180 | 0 | - | + | 0 | + | |
| 142 | 180 | 0 | - | + | 0 | 0 | |
| 143 | 180 | 0 | - | + | 0 | - | |
| 79 | 180 | 0 | - | + | - | + | |
| 144 | 180 | 0 | - | + | - | 0 | |

*Figure 19c*

| | | | | | | | |
|---|---|---|---|---|---|---|---|
| 145 | 180 | 0 | - | + | - | - | |
| 146 | 180 | 0 | - | 0 | + | + | |
| 147 | 180 | 0 | - | 0 | + | 0 | |
| 148 | 180 | 0 | - | 0 | + | - | |
| 149 | 180 | 0 | - | 0 | 0 | + | |
| 150 | 180 | 0 | - | 0 | 0 | 0 | |
| 151 | 180 | 0 | - | 0 | 0 | - | |
| 152 | 180 | 0 | - | 0 | - | + | |
| 153 | 180 | 0 | - | 0 | - | 0 | |
| 154 | TPW | 0 | - | 0 | - | - | |
| 155 | TPW | 0 | - | - | + | + | |
| 156 | TPW | 0 | - | - | + | 0 | |
| 157 | TPW | 0 | - | - | + | - | |
| 158 | TPW | 0 | - | - | 0 | + | |
| 159 | TPW | 0 | - | - | 0 | 0 | |
| 160 | TPW | 0 | - | - | 0 | - | |
| 161 | TPW | 0 | - | - | - | + | |
| 162 | TPW | 0 | - | - | - | 0 | |
| 163 | TPW | 0 | - | - | - | - | |
| 164 | 180 | - | + | + | + | + | |
| 165 | 180 | - | + | + | + | 0 | |
| 166 | 180 | - | + | + | + | - | |
| 167 | 180 | - | + | + | 0 | + | |
| 168 | 180 | - | + | + | 0 | 0 | |
| 169 | 180 | - | + | + | 0 | - | |
| 170 | 180 | - | + | + | - | + | |
| 171 | 180 | - | + | + | - | 0 | |
| 172 | 180 | - | + | + | - | - | |
| 173 | 180 | - | + | 0 | + | + | |
| 174 | 180 | - | + | 0 | + | 0 | |
| 175 | 180 | - | + | 0 | + | - | |
| 176 | 180 | - | + | 0 | 0 | + | |
| 177 | 180 | - | + | 0 | 0 | 0 | |
| 178 | 180 | - | + | 0 | 0 | - | |
| 179 | 180 | - | + | 0 | - | + | |
| 180 | 180 | - | + | 0 | - | 0 | |
| 181 | 180 | - | + | 0 | - | - | |
| 182 | 180 | - | + | - | + | + | |
| 183 | 180 | - | + | - | + | 0 | |
| 184 | 180 | - | + | - | + | - | |
| 185 | 180 | - | + | - | 0 | + | |
| 186 | 180 | - | + | - | 0 | 0 | |
| 187 | 180 | - | + | - | 0 | - | |
| 188 | 180 | - | + | - | - | + | |
| 189 | 180 | - | + | - | - | 0 | |
| 190 | 180 | - | + | - | - | - | |
| 191 | 180 | - | + | + | + | + | |
| 192 | 180 | - | 0 | + | + | 0 | |
| 193 | 180 | - | 0 | + | + | - | |
| 194 | 180 | - | 0 | + | 0 | + | |
| 195 | 180 | - | 0 | + | 0 | 0 | |
| 81 | 180 | - | 0 | + | 0 | - | |
| 196 | 180 | - | 0 | + | - | + | |
| 197 | 180 | - | 0 | + | - | 0 | |

*Figure 19d*

| | | | | | | | |
|---|---|---|---|---|---|---|---|
| 198 | 180 | - | 0 | + | - | - | |
| 199 | 180 | - | 0 | 0 | + | + | |
| 200 | 180 | - | 0 | 0 | + | 0 | |
| 201 | 180 | - | 0 | 0 | + | - | |
| 202 | 180 | - | 0 | 0 | 0 | + | |
| 203 | 180 | - | 0 | 0 | 0 | 0 | |
| 204 | 180 | - | 0 | 0 | 0 | - | |
| 205 | 180 | - | 0 | 0 | - | + | |
| 206 | 180 | - | 0 | 0 | - | 0 | |
| 207 | 180 | - | 0 | 0 | - | - | |
| 208 | 180 | - | 0 | - | + | + | |
| 209 | 180 | - | 0 | - | + | 0 | |
| 210 | 180 | - | 0 | - | + | - | |
| 211 | 180 | - | 0 | - | 0 | + | |
| 212 | 180 | - | 0 | - | 0 | 0 | |
| 213 | 180 | - | 0 | - | 0 | - | |
| 214 | 180 | - | 0 | - | - | + | |
| 215 | 180 | - | 0 | - | - | 0 | |
| 216 | 180 | - | 0 | - | - | - | |
| 217 | 180 | - | - | + | + | + | |
| 218 | 180 | - | - | + | + | 0 | |
| 219 | 180 | - | - | + | + | - | |
| 220 | 180 | - | - | + | 0 | + | |
| 221 | 180 | - | - | + | 0 | 0 | |
| 222 | 180 | - | - | + | 0 | - | |
| 223 | 180 | - | - | + | - | + | |
| 224 | 180 | - | - | + | - | 0 | |
| 225 | 180 | - | - | + | - | - | |
| 226 | 180 | - | - | 0 | + | + | |
| 227 | 180 | - | - | 0 | + | 0 | |
| 228 | 180 | - | - | 0 | + | - | |
| 229 | 180 | - | - | 0 | 0 | + | |
| 230 | 180 | - | - | 0 | 0 | 0 | |
| 231 | 180 | - | - | 0 | 0 | - | |
| 232 | 180 | - | - | 0 | - | + | |
| 233 | 180 | - | - | 0 | - | 0 | |
| 234 | 180 | - | - | 0 | - | - | |
| 235 | 180 | - | - | - | + | + | |
| 236 | 180 | - | - | - | + | 0 | |
| 237 | 180 | - | - | - | + | - | |
| 238 | 180 | - | - | - | 0 | + | |
| 239 | 180 | - | - | - | 0 | 0 | |
| 240 | 180 | - | - | - | 0 | - | |
| 241 | 180 | - | - | - | - | + | |
| 242 | 180 | - | - | - | - | 0 | |
| 243 | 180 | - | - | - | - | - | |

*Figure 19e*

*Figure 21*
User Interface
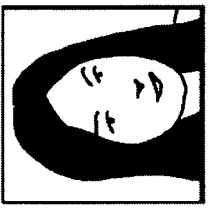

IMAGING SYSTEM AND METHOD FOR PHYSICAL FEATURE ANALYSIS

CROSS-REFERENCE TO RELATED APPLICATION(S)

None.

FIELD OF THE INVENTION

The present invention generally relates to an imaging system and method for body feature analysis, such as the condition of skin or hair, and more particularly, to an imaging system and method for capturing, processing, and analyzing attributes of body features, such as skin or hair, so that care product recommendations can be evaluated and provided to address conditions identified by the image analysis and related data.

BACKGROUND OF THE INVENTION

Due to an increase in awareness and desire for healthier and longer life, research and innovation in healthcare and longevity of human body physical features, such as skin and hair, have been conducted for decades. One recent aspect of the research and innovation is to have an imaging system to enhance study of attributes of physical features and to aid in planning care for conditions identified by the image analysis.

One form of imaging system is a handheld magnifying apparatus that provides a video image to a screen, at which a dermatologist or other professional can study the details shown in the image to evaluate conditions and make treatment recommendations. For example, U.S. Pat. No. 5,442,489, titled "Magnifying Observation Apparatus".

It is also known to provide software that accepts as input certain skin condition survey answers and to provide a recommendation for skin treatment products that address the conditions and a subject's expressed preferences. For example, Nu Skin International Inc. of Provo, Utah offers a Nu Skin Regimen Optimizer™ software program.

As digital image processing has become more widespread, systems have been developed for capturing digital skin images and using computer means to analyze the digital images, e.g., U.S. Pat. No. 6,571,003 B1 and U.S. Patent Application Publication 2004/0218810.

SUMMARY OF THE INVENTION

The present invention provides a PDA-based imaging system that captures images of skin or other physical features, performs real-time analysis of the images to develop summary rating values, stores the image files, prepares care regimen recommendations to address conditions identified by the image analysis, and provides a user interface allowing the user to control each of these functions.

In one embodiment, the system for capturing and analyzing images of body features to identify treatments, comprises a base unit with a processor and a display; an image management software component for presenting on the display a user interface to prompt a user to capture images in preselected locations on a body and to receive captured image data; at least two light sources under control of the user interface providing light following first and second light paths from the respective light sources to an object plane or the plane of an imaging station, each said light path having a significant portion of its light directing at a grazing angle onto the object plane at about ten to about thirty degrees and the first and second light paths when projected onto the object plane intersecting at an angle of at least sixty degrees; an image sensor for receiving light from the light sources that is reflected from the surface of a body feature located on the object plane and for producing pixel image data representing the body feature; and a rating software component receiving the pixel image data from the image sensor and configured to mimic the judgment of a dermatologist to provide a rating vector representing the condition of three or more attributes of the body feature represented by the pixel image data.

These and other features and advantages of the present invention will become apparent to those skilled in the art from the following detailed description, wherein illustrative embodiments of the invention are shown and described, including best modes contemplated for carrying out the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 18 is a set of tables showing an exemplary scoring range and set of sample scores on that range and further showing how a set of scoring weights is defined in one embodiment of the invention.

FIGS. 19a-19e are a table showing how various combinations of range values developed by assigning normalized raw scores to predefined ranges can be associated with particular product regimens.

FIG. 21 shows two screens from a user interface generated by the application software shown in FIG. 15.

DETAILED DESCRIPTION

The present invention provides a computer-based imaging system that captures images of skin or other physical features, performs real-time analysis of the images to develop summary attribute measurement values, stores the image files, relates care regimen recommendations to conditions identified by the image analysis and related data, and provides a user interface allowing the user to control each of these functions. In one embodiment, a PDA provides the computer processing needed. A variety of other processor platforms could be used, including laptop computers and sufficiently powerful handheld messaging and telephone devices.

Hardware

As seen in FIGS. 1-5, a PDA-based imaging system 100 comprises a PDA 102 with software for image capture and processing, an optics/imaging attachment 104 with imaging sensor 602 and coordinated illumination (see FIG. 6b) for capturing images for study of an attribute of a physical feature, and a flash card slot printed circuit board assembly (PCBA) 106 serving primarily as a connection interface and buffer between the PDA 102 and the optics/imaging attachment 104.

Optics/Imaging Attachment

Figure 6A:
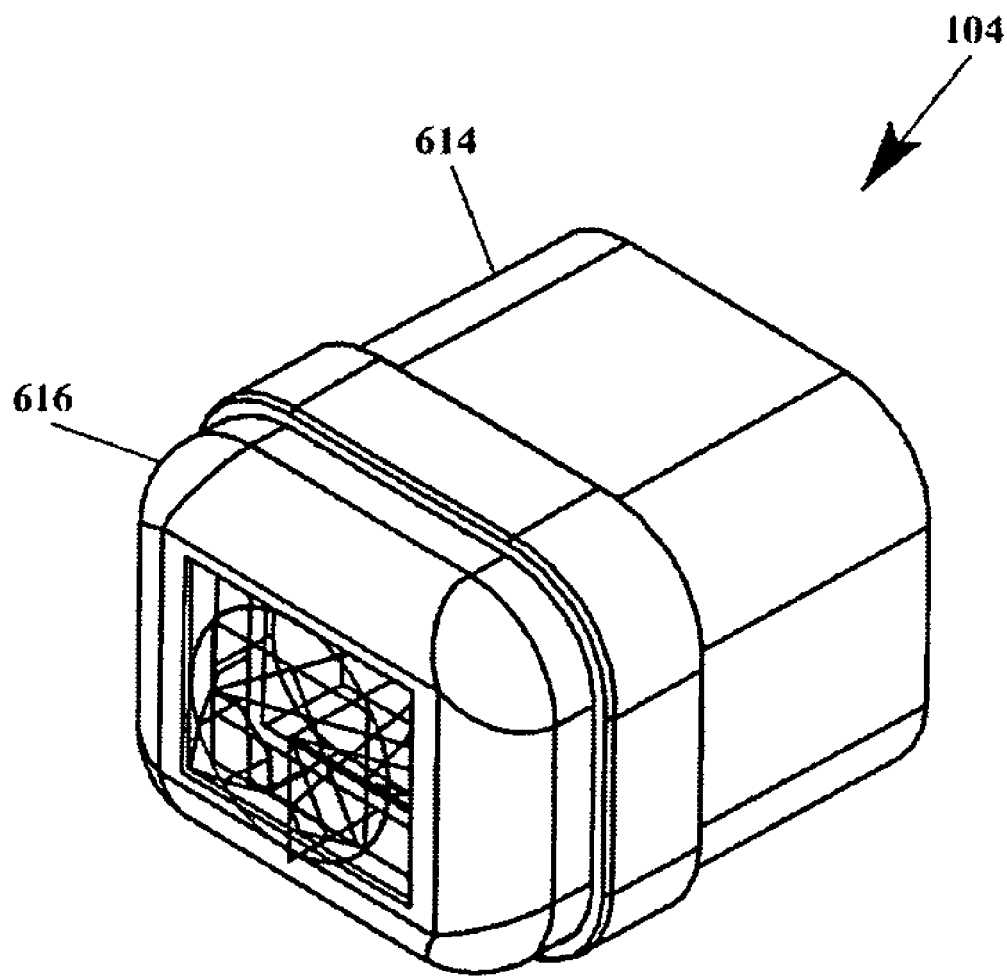
FIGS. 6a and 6b illustrate perspective assembled and exploded views, respectively, of one embodiment of the optics/imaging attachment as shown in FIG. 4.
Figure 6B:
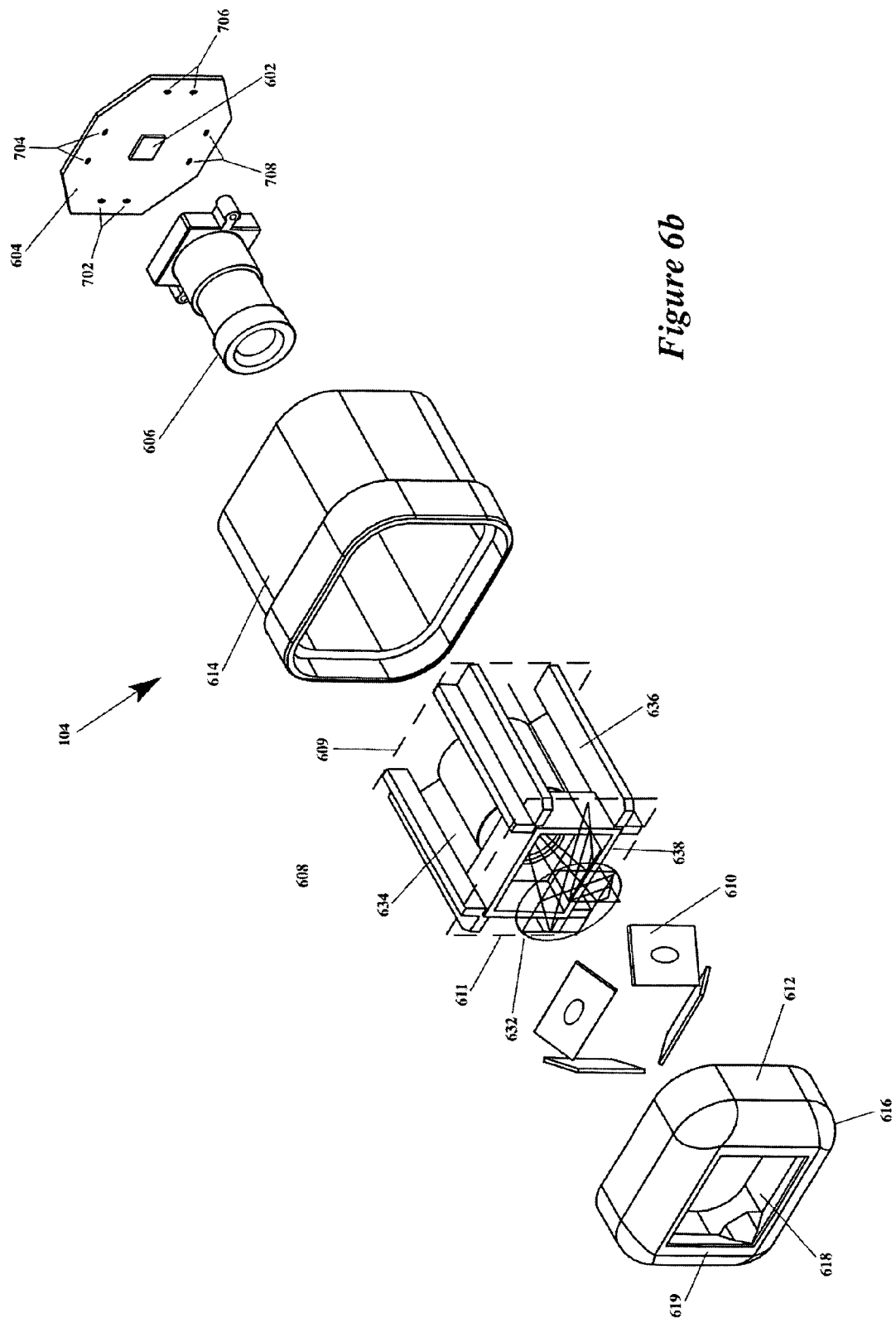

As shown in FIGS. 6a and 6b, optics/imaging attachment 104 includes a circuit board 604 with a CMOS image sensor chip 602, and light sources, such as sets of paired LEDs 702, 704, 706, 708 (see FIG. 7), with one pair on each of the four (left, top, right and bottom) sides of circuit board 604. It is appreciated that the LED implementation may include chip-on-board, surface mount, or any other suitable light source implementation. Attachment 104 also has an optics assembly 606 with lenses fixed in a lens holder, a light baffle 608, a set of reflector elements 610 mounted in a reflector fixture 612 and each associated with a respective pair of LEDs, and an optics housing 614. As seen in FIG. 6a, the optics housing 614 and the reflector fixture 612 are coupled to house the other components of the attachment 104. The reflector fixture 612 has a generally rectangular aperture 618 that is used to frame an area on an object to be imaged. The outer edges of the aperture 618 define an object plane 619, where the area of the body to be imaged is placed for image capture. It will be appreciated that the configuration and arrangement of the optics/imaging attachment 104 may vary depending on the desired use. For example, an optics/imaging attachment for imaging hair, different skin areas or other body features may be of a different configuration than an optics/imaging attachment for imaging facial skin. For veterinary uses to study the skin, hair or other body features of animals, other attachment configurations suited to the different physical attributes of these subjects are possible.

Optics/Imaging Attachment—Image Sensor

The CMOS image sensor chip 602 is a sensor chip that senses light impinging on a grid of individual pixel locations and can be controlled to deliver read-out of digital information sensed at each pixel. For example, the sensor 602 may be the model OV9650 sensor chip from OmniVision Technologies Inc. of Sunnyvale, Calif. The OV9650 is a camera and image sensor that is controlled through a Serial Camera Control Bus (SCCB) interface 1470 (see discussion of FIGS. 14a, 14b) defined by the supplier. Per OmniVision's description of the SCCB interface, the OV9650 is a slave device of the companion back-end interface, the SCCB interface, which asserts as the master. Accordingly, the image sensor chip 602 will receive control signals from the PDA and PCBA components of the device and will provide image data at its outputs for reading by the PCBA 106. The image capture is driven and controlled by signals coming in over the connector interface 1408 of the PCBA 106 leading to the connector 1428 (see FIG. 14a) of the optics/imaging attachment 104. In one embodiment, the "master" for the image sensor chip 602, controlling signals to the SCCB interface of the sensor chip 602 is the application software stored on the PDA 102 and executing on the PDA's microprocessor 1402, as further described below in connection with FIG. 14b.

Optics/Imaging Attachment—Illumination and Optics

Figure 13:
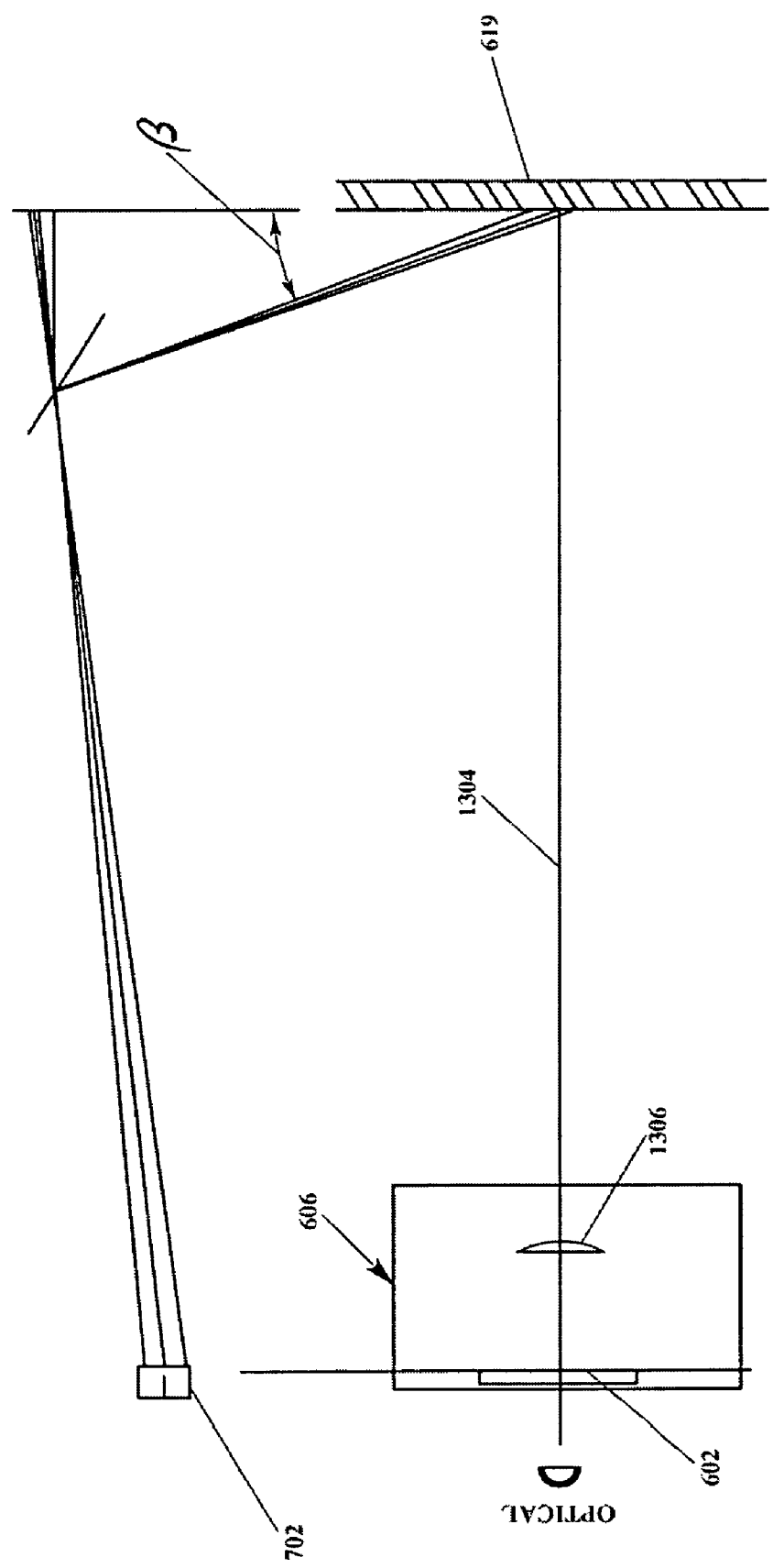
FIG. 13 illustrates a schematic view of an exemplary LED light path within the optics/imaging attachment.

The optics/imaging attachment 104 provides illumination to the object plane 619 (see FIG. 6b and FIG. 13) and the surface of an object located in the object plane 619. It has a shaped nosepiece 616 (see FIGS. 6a, 6b) for framing the object plane 619 and keeping most ambient light away from the surface of the object to be imaged. The attachment 104 has an optical axis 1304 defining the center of a path for receiving light reflected from the surface of the object to be imaged. It further has optics, such as one or more lenses 1306 held in frames of optics assembly 606 (see FIG. 6b), for focusing light from the surface of the object on the image sensor 602.

Figure 7:
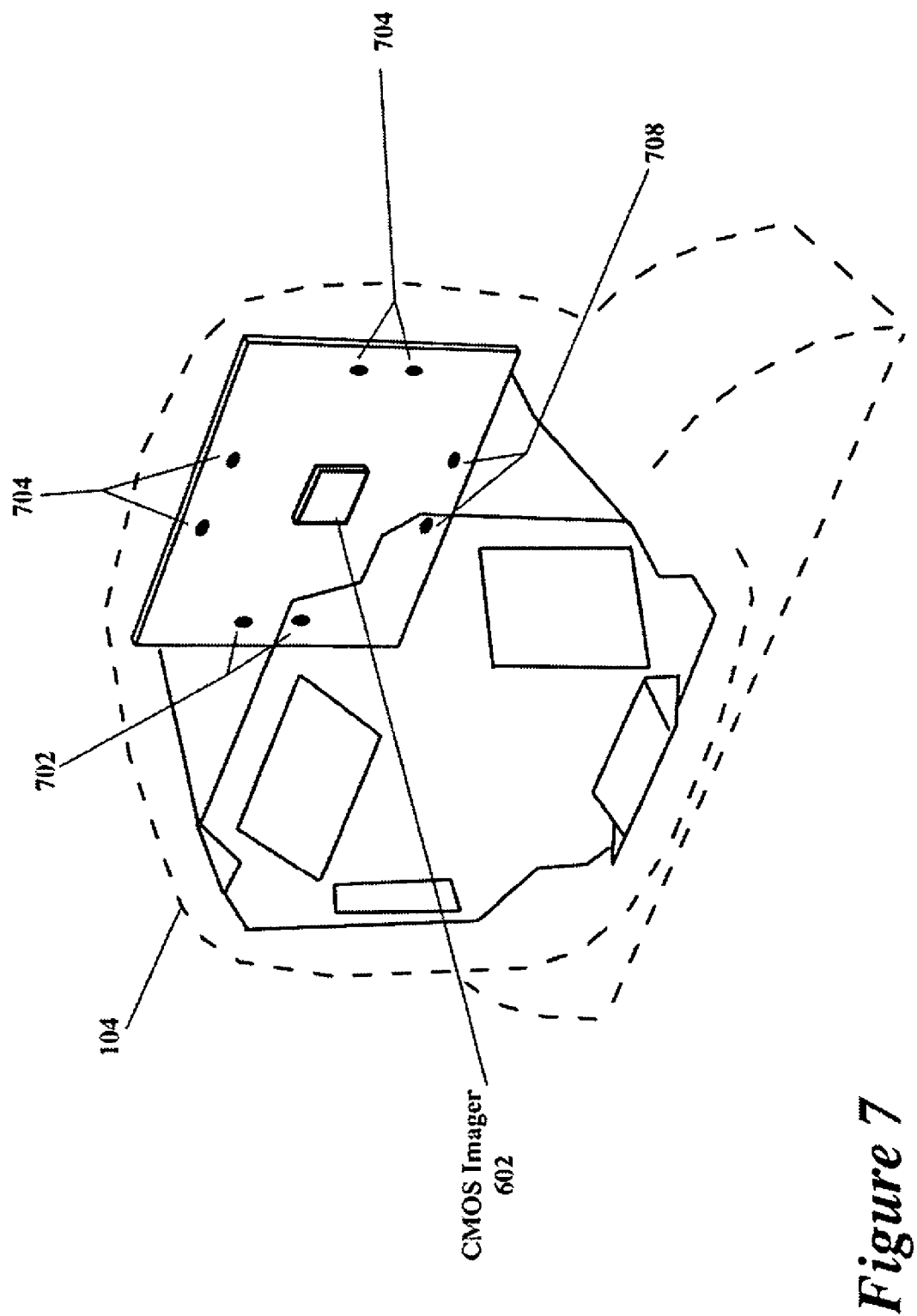
FIG. 7 illustrates a perspective and focused/background-shaded view of one embodiment of the optics/imaging attachment having a plurality of LEDs mounted on a printed circuit board.
Figure 8:
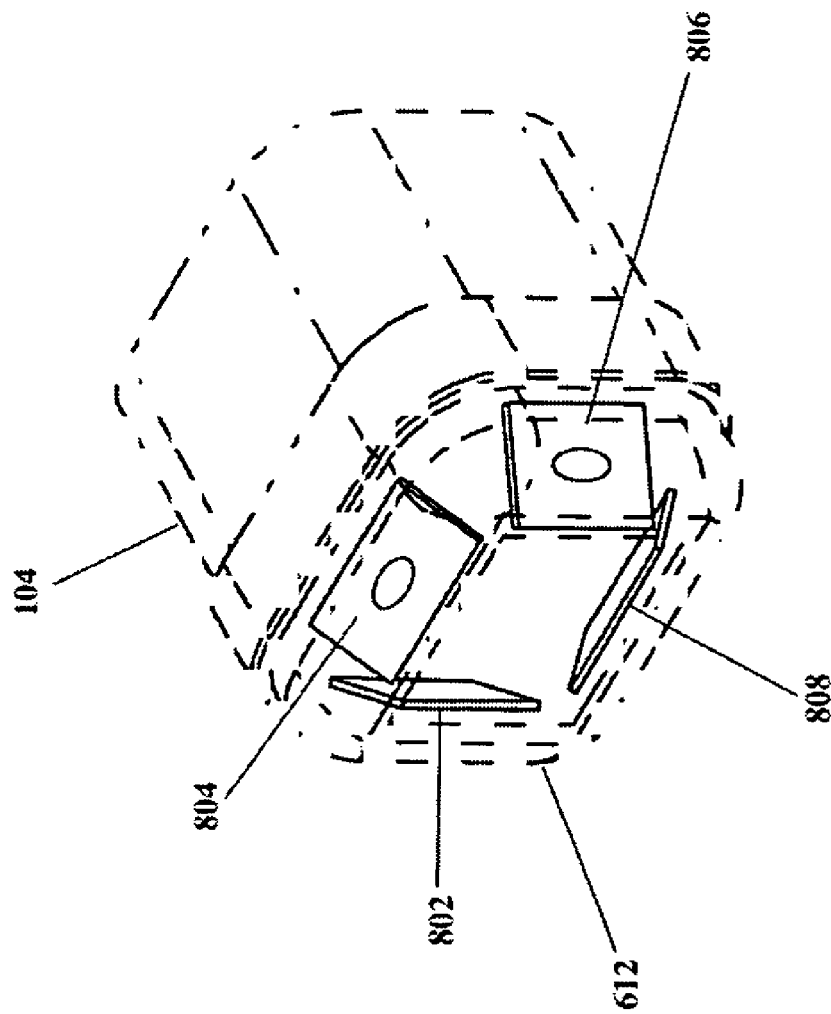
FIG. 8 illustrates a perspective and focused/background-shaded view of one embodiment of the optics/imaging attachment having a plurality of light path mirrors that are associated with the respective LEDs.
Figure 9:
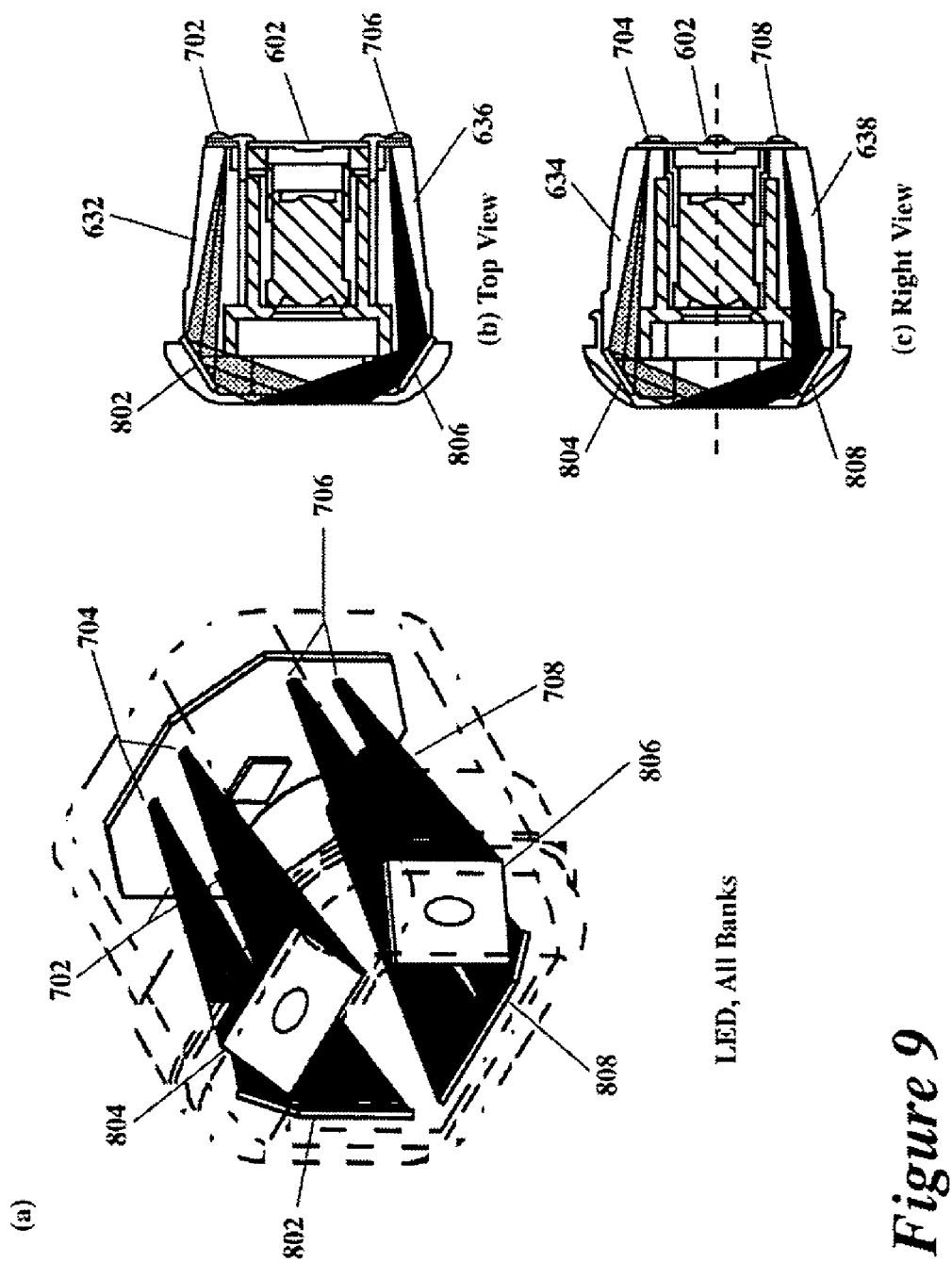
FIGS. 9a-9c illustrate perspective, top, and right views of one embodiment of the optics/imaging attachment showing light paths when all LEDs are activated.
Figure 10:
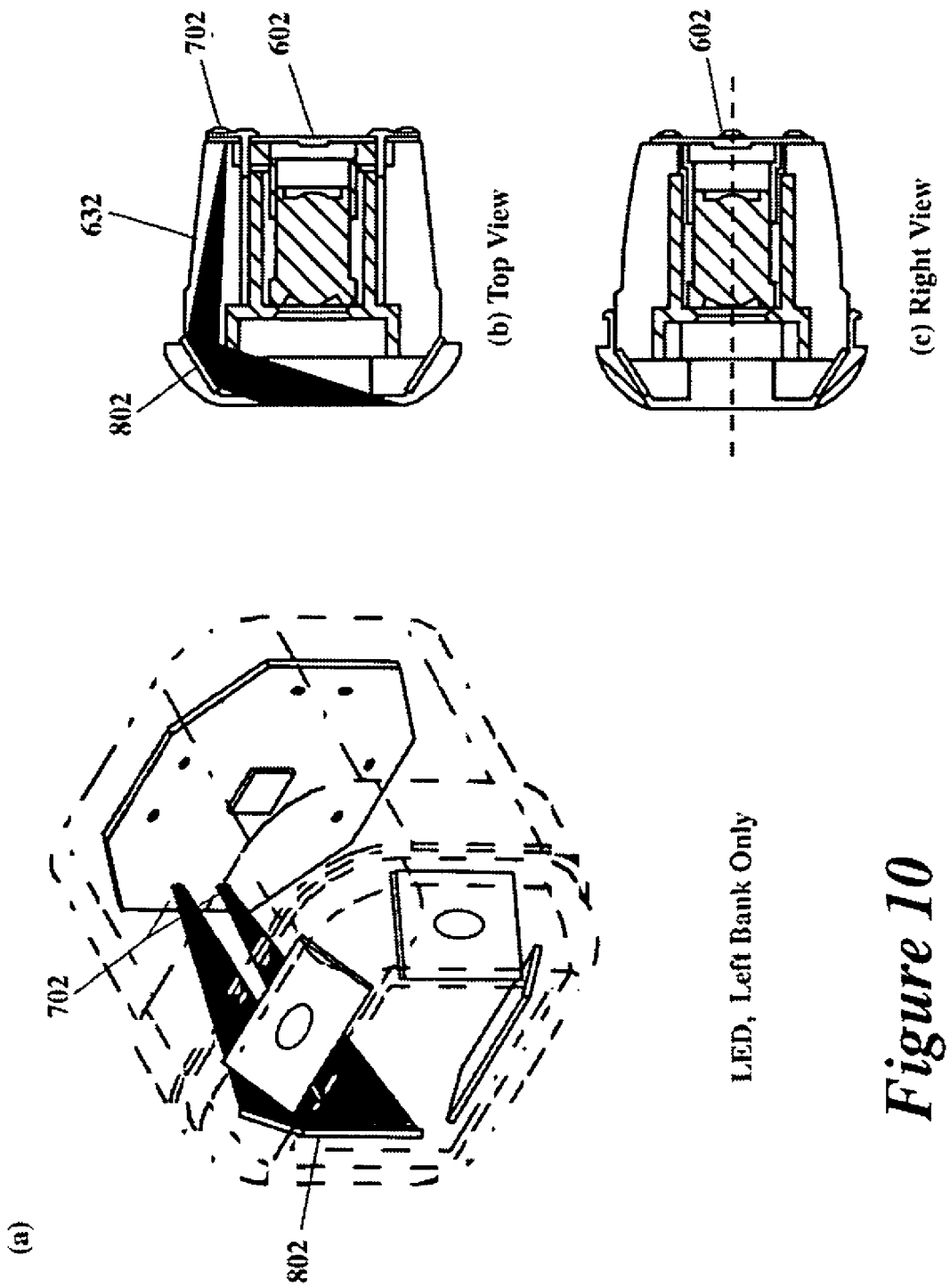
FIGS. 10a-10c illustrate perspective, top and right side views of one embodiment of the optics/imaging attachment showing light paths when only left side LEDs are activated.
Figure 11:
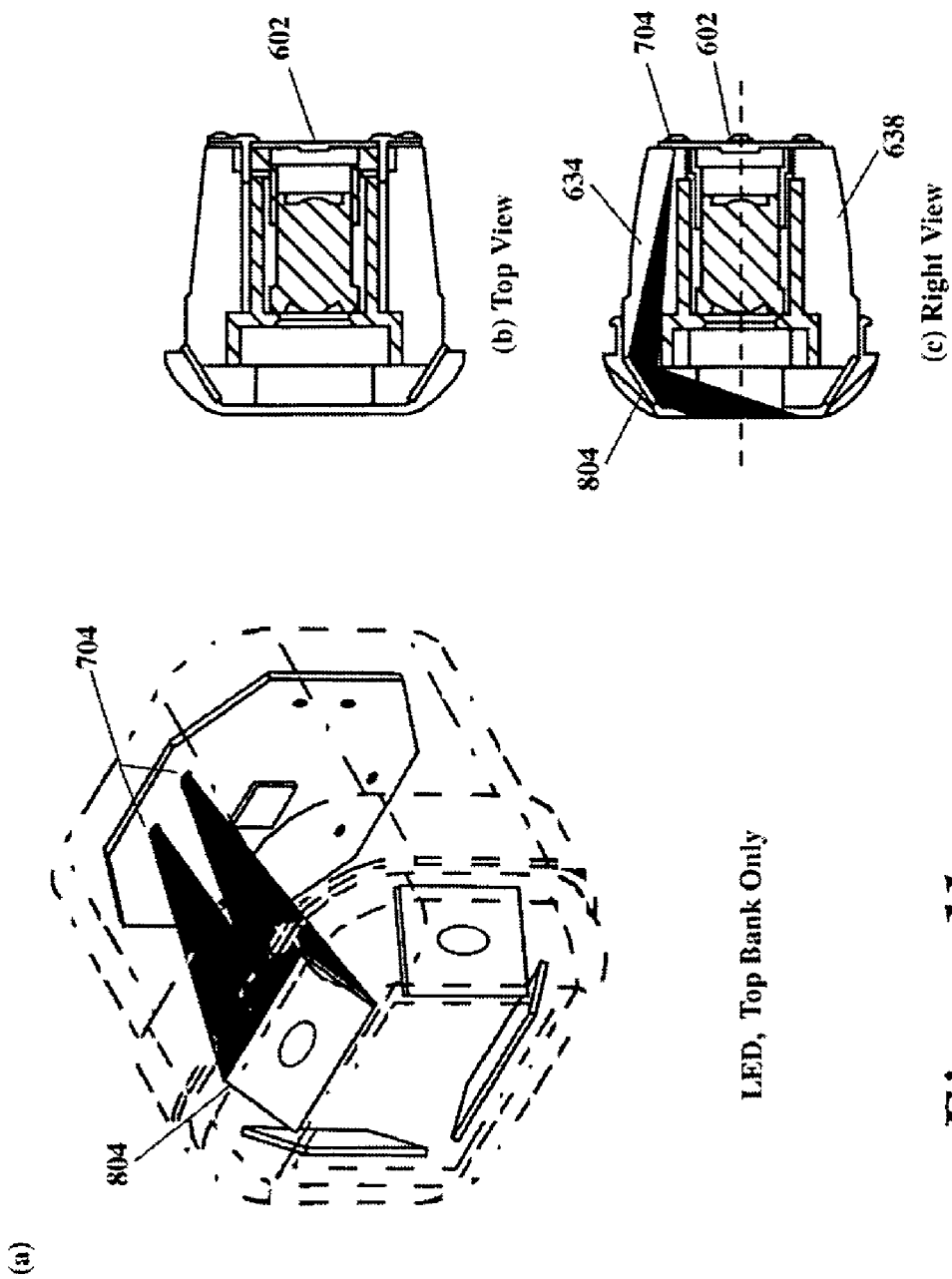
FIGS. 11a-11c illustrate perspective, top and right side views of one embodiment of the optics/imaging attachment showing light paths when only top LEDs are activated.
Figure 12:
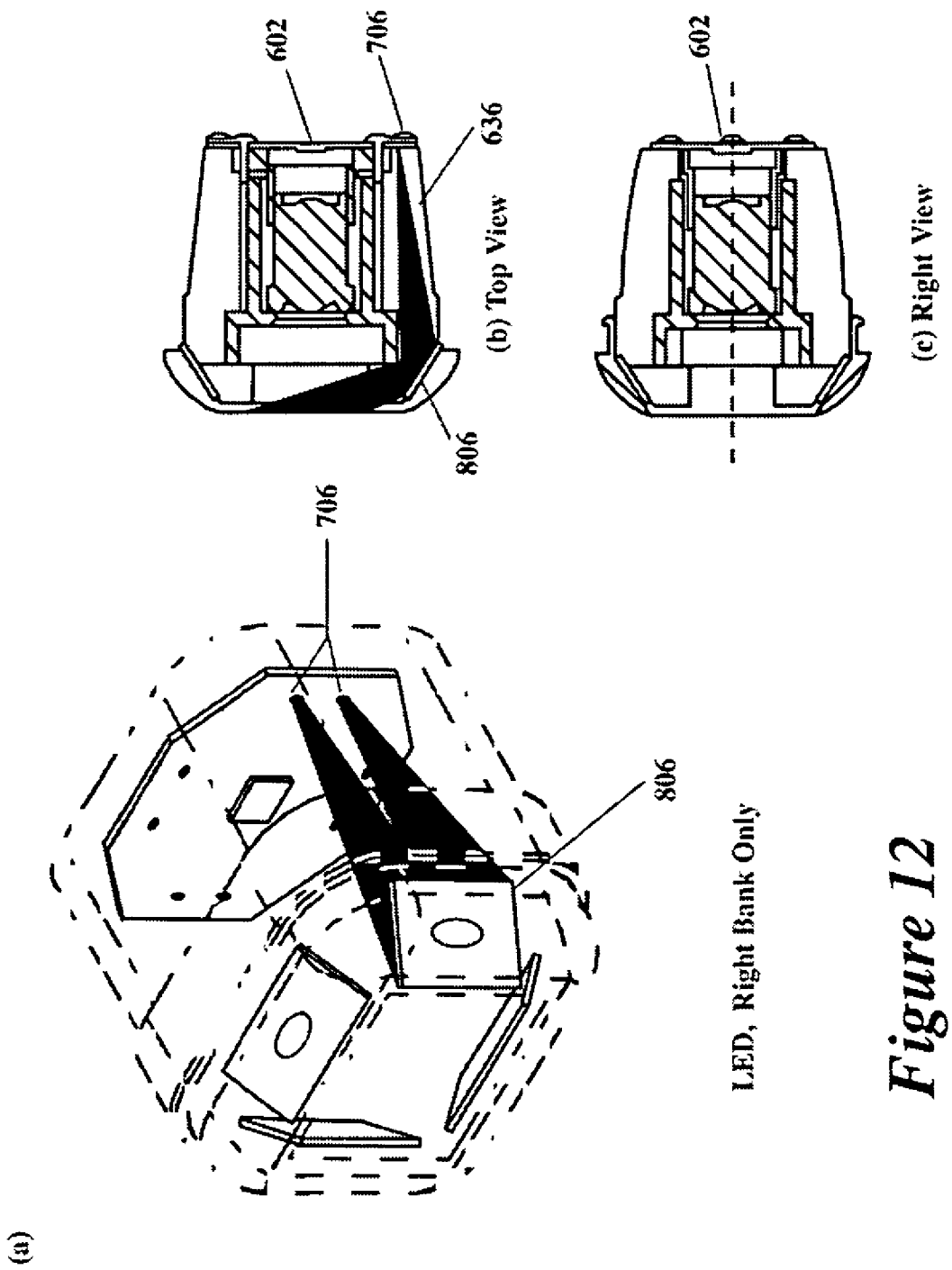
FIGS. 12a-12c illustrate perspective, top and right side views of one embodiment of the optics/imaging attachment showing light paths when only right side LEDs are activated.

In one embodiment, illumination light sources are a set of LEDs with corresponding reflective elements 610 to direct the light to the object plane 619. As shown in FIG. 7, there may be eight LEDs, in four pairs 702 (left), 704 (top), 706 (right), 708 (bottom), with associated reflective components 802, 804, 806, 808, such as mirrors, prisms, or any other suitable light diffracting (light gratings)/light redirecting/light reflecting materials/technologies, that are mounted in reflector fixture 612 and angle-oriented to provide a desired type of illumination when all or a subset of LED pairs 702-708 are powered. In particular, each pair of LEDs and its associated reflective component is positioned to provide illumination from one of the top, bottom, right side or left side of the surface 1302 to be imaged. Moreover, the positioning is selected so that illumination from each side is provided with a specified grazing angle (β) on the object plane 619, for example, about 20° (20 degrees). For producing images with distinct shadows to reveal surface variations in skin, a grazing angle of about 10° (10 degrees) has been found effective; however, the actual grazing angle of at any point on the area of human skin or other body features to be illuminated will vary, based on the irregularities in that surface and the dispersion of the light rays. Thus, a range for the grazing angles from about 10° (10 degrees) to about 30° (30 degrees) is accommodated for all LED-reflector element combinations by the design of attachment 104.

The light baffle 608, made of a dark, light absorbing material, helps reduce stray light and also to deliver the light flux from the LEDs to the object plane 619 at the desired grazing angle. The light baffle 608 receives at its entry plane 609 light flux from each of the LED light sources 702-708. The baffle 608 helps define the light flux from each LED 702-708 to near its exit plane 611, where the light flux from respective LEDs hits its corresponding reflector element 610 and is directed to the object plane 619. The interior surfaces of baffle 608 absorb stray light so as to prevent light from any LED traveling directly to the object plane 619; instead, substantially all light arrives at the object plane 619 only after reflection from one of the associated reflective elements 802-808, which largely establishes the grazing angle of the light on the object plane 619.

The top, bottom, right and left sides of the exterior of the baffle 608 define first through fourth channels 632, 634, 636, 638 for the light flux from the respective LEDs 702-708 to travel to the reflector components 610. Each of the channels 632, 634, 636, 638 blocks substantially all light from its corresponding light source except for a flux of light emitted generally in the direction of the object plane 619 and thus helps deliver light rays to the associated reflector element 802-808 along four optical paths generally parallel to the optical axis 1304, each associated with one pair of LEDs. The light baffle 608 also defines at its center a path for the light reflected away from the object plane 619 to travel to the lenses that focus the reflected light on the image sensor 602 and make possible a magnified image of surface located at the object plane 619.

The LED pairs 702-708 may provide light of any wavelength, visible or invisible. In one embodiment each LED provides "white" light, including substantially all wavelengths of the visible light spectrum. For example, the Part No. HMF 0603WH00BC, an LED from Xiamen Hualien Electronics Co. Ltd. of Fujian, China may be used. It emits light in broad range of visible wavelengths. The angle of the cone of emitted light may be broad or narrow, as long as sufficient light can be delivered through the light baffle 608 and by reflection from the reflective elements 802-808 that aim the reflected light onto the imaged surface at the object plane 619. The light output from each LED is about 400 milli-lumens in one embodiment.

The reflective elements 802-808 may be mirrors for simplicity and ease in cleaning, although the metallic layer causes some loss of light energy. Alternatively, they may be prisms, shaped and positioned relative to the incoming LED light so as to use total internal reflection of such light to direct the light onto the imaged surface 1302. A properly positioned prism has very little light loss and thus is more efficient than a mirror. Delivery of light from the LEDs by one or more light fibers is also possible. Further, if it is desired to introduce polarization or other treatment of the light sources, one or more of the reflector elements may have an associated filter or other suitable optical element. The elements may induce polarization or other effects that aid imaging.

The light reaching the object plane 619 is partially absorbed and partially reflected in the direction of the optical axis 1304 toward the image sensor 602. The lens(es) 1306 along the optical axis 1304 may have an aperture to effect an F-stop in the camera lens. The F-stop of the lens aperture is selected to provide a depth of field that covers a sufficient distance (approximately 0.5 inches) on either side of the object plane 619 framed by the nosepiece aperture 618. This is desirable, because when soft tissue or tissue with irregular contours is imaged, some portions of the tissue may be a greater distance from the image sensor 602 than the object plane 619 or may be at a lesser distance, if tissue is pressed against or into the aperture 618. Sufficient depth of field helps simplify the device and its use, by permitting an instrument in which the lens' positions are fixed and require no focus adjustment to produce the desired image, even when tissue is not exactly in the object plane 619.

One objective of the illumination arrangement is to provide illumination of different types to produce images from the image sensor chip 602 that are effective to reveal particular attributes of the different physical features imaged. When skin is imaged, examples of attributes desirable to reveal by illumination and to detect in the captured images are "discoloration", "oiliness/shine", "lines/wrinkles", "texture", and "pore size", etc. Pursuing images appropriate for observing and accurately measuring the condition of these attributes is guided by the following dermatologist-defined considerations:

a. Lines/Wrinkles—Outer Eye Area

The skin of the outer eye area is the thinnest on the body and the most likely to show early signs of fine wrinkling. In damaged or aged skin, this area shows many fine lines that are long and well defined.

b. Texture—Center Cheek Area

The central cheek is the broadest expanse of skin on the face with the easiest location to spot skin texture irregularities. A rough texture has many angular ridges and elevated edges that may look dry, flaky and irregular in elevation.

c. Pores—two locations, cheek area close to the nose and outer cheek area, side of face.

Pore size varies over the face. The largest pores are on the nose and the cheek area closest to the nose, while the smallest pores are found on the side of the face. When comparing these two areas, if the pores are small and are similar in number at both areas, near the nose and on the side of the face, the skin can be said to have fine pore structure.

d. Coloration—four locations: side outer forehead, outer cheek area, below and away from the corner of the mouth and the inner forearm.

Skin color depends on the amount of blood flow present beneath the skin and the ability of the skin to tan. An overall assessment of facial skin color involves consistency in color perception from four locations on the face. Closely similar values for all areas describes an even coloration. If the coloration value of the forearm is different from the coloration values for the remaining three areas, this suggests that the skin on the face is exposed to UV light and may indicate that, although the other three areas are close in coloration values and represent an even coloration, continued exposure to UV light may lead to uneven coloration in the three facial areas.

e. Oil/shine—two locations, center forehead and below the corner of the mouth.

Oily skin is most commonly observed on the central forehead and on the lateral chin. Both areas require assessment for an accurate description of facial oil production. If both areas exhibit similar oil production, the skin may be classified as oily. If the two values vary significantly from each other, then the skin can be classified as combination skin. Very little oil production in these areas, and the skin may be considered dry.

Thus, it is desirable to illuminate skin located at specific different areas on the body, including wrist, forehead, cheek, skin, eye corner, or other specific locations and to illuminate these different areas in different ways for different purposes. To do this effectively, the present device makes each LED or each pair of LEDs 702-708 selectively activatable, based on control signals and power from the PDA 102 and/or PCBA 106. In one embodiment, the power delivered to, and thus the illumination intensity delivered from, each LED in pairs 702-708 is constant. In another embodiment, it is controllable over a range sufficient to provide good images, including accommodating different skin coloration and avoiding saturation of the image sensor 602. The various control options may be desirable when an optics/image attachment is used for more than one kind of imaging, e.g., skin and hair.

FIGS. 9a-9c, 10a-10c, 11a-11c, and 12a-12c illustrate exemplary light paths when all or some of the LEDs 702-708 are activated to deliver light flux through the baffle 608. The LED-reflector element combinations and the baffle 608 are configured so that the light sources 702-708 deliver light flux to the object plane 619 along substantially separate paths from four different directions. In particular, top and bottom LEDs 704, 708 and their respective reflectors 804, 808 deliver light flux from two directions that are generally parallel but opposite in their direction of travel, when both LED pairs 704, 708 are illuminated and the vector of light travel from each is projected onto the object plane 619. Left and right hand LEDs 702, 706, when illuminated, form a similar opposed pair of light sources, and the light vectors from this opposed pair of LEDs are also substantially orthogonal to the light vectors from top and bottom LEDs 704, 708, again when all light vectors are projected onto the object plane 619.

The LEDs deliver light as required for each of the following situations. In one embodiment, the "discoloration" skin attribute is captured in images acquired with all of the LEDs 702-708 being activated (light from all reflective elements). The "oiliness/shine" skin attribute also is captured in images acquired with all of the LEDs 702-708 being activated. The "lines/wrinkles" skin attribute is captured in images acquired with only top LEDs 704 being activated, to provide light (from reflective element 804 only) that is largely orthogonal to the longitudinal extent of the most common wrinkles. The "texture" skin attribute is captured in images acquired with all of the LEDs 702-708 being activated. The "pore size" skin attribute is captured in images acquired with either the right LEDs 706 or left LEDs 702 only, depending on whether the right-side or left-side of the face is being imaged. In either situation, the light path from the LEDs selected for illumination of pores is directed so that the light traveling to the imaged area 1302 is traveling away from the nose, after it is reflected by the corresponding reflector element 806 or 802.

One objective of the different light sources and light paths is to enable selection of light from a single direction (to accentuate shadows) or light from two or more directions, to adjust the contrast of the image. When light from two or more directions is desired, it is useful to have different relative orientations between the light rays incoming to the imaged surface 1302. The relative orientations can be viewed in terms of the angle between the vectors representing incoming light when these vectors are projected onto the object plane 619. With that viewpoint, it is desired to be able to select light from two different directions.

PDA Platform

The PDA 102 may be any PDA with sufficient memory and processing power to handle the operating system and application software of the present invention, with a display for presenting both a user interface and images captured or to be captured and with a reasonable set of navigational controls to allow a user to control all native PDA functions but also to provide inputs that are called for by the user interface of the applications. For example, the PDA may be a Dell Axim x51.

Figure 1:
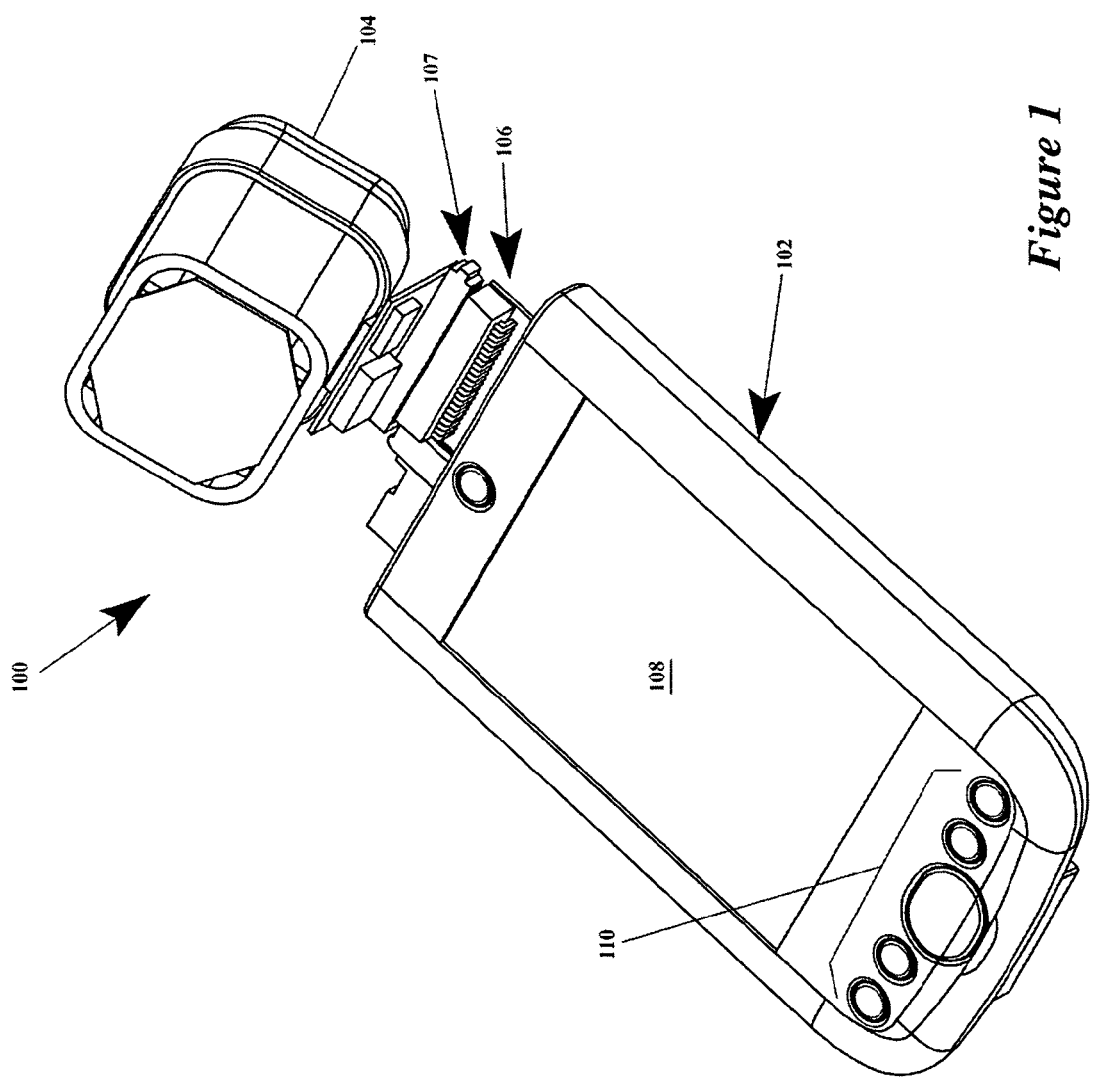
FIG. 1 illustrates a perspective view of one embodiment of a PDA-based imaging system in accordance with the principles of the present invention.
Figure 2:
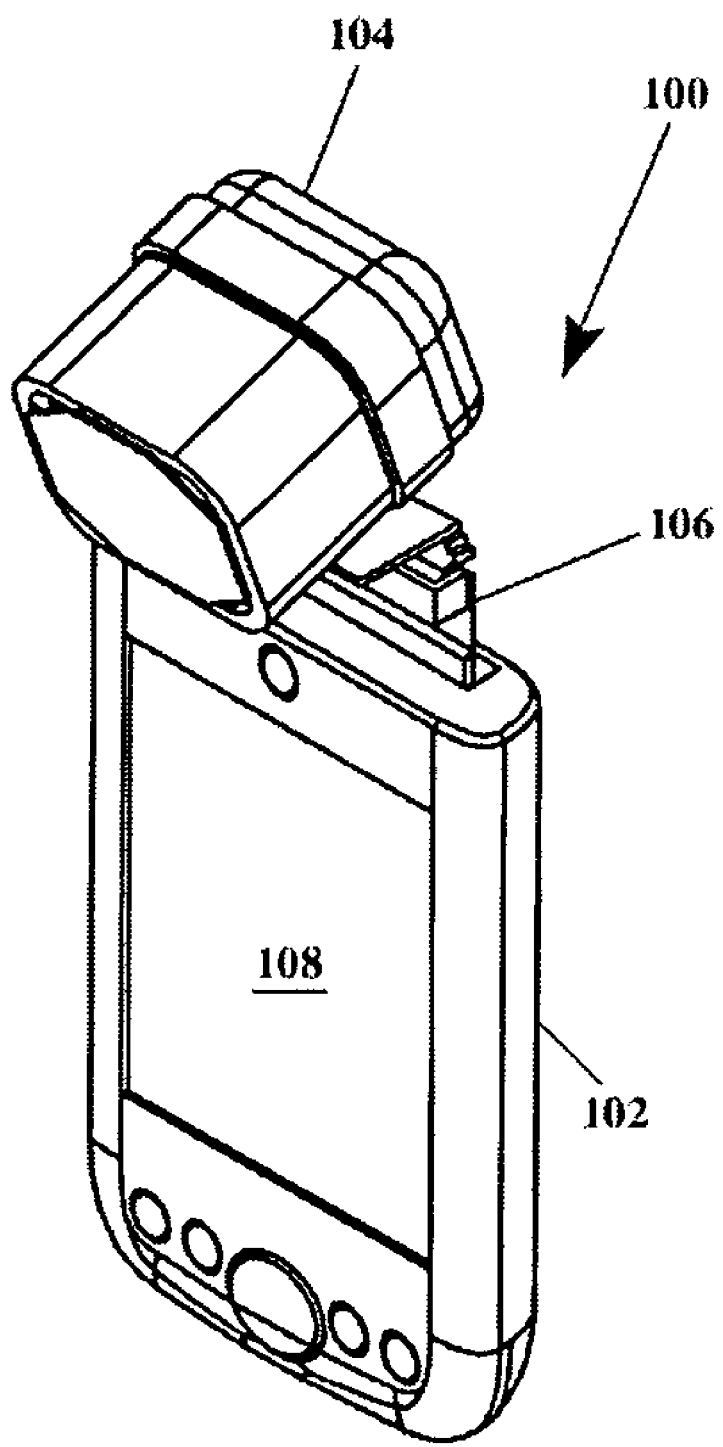
FIGS. 2 and 3 illustrate different perspective views of one embodiment of the PDA-based imaging system as shown in FIG. 1.
Figure 3:
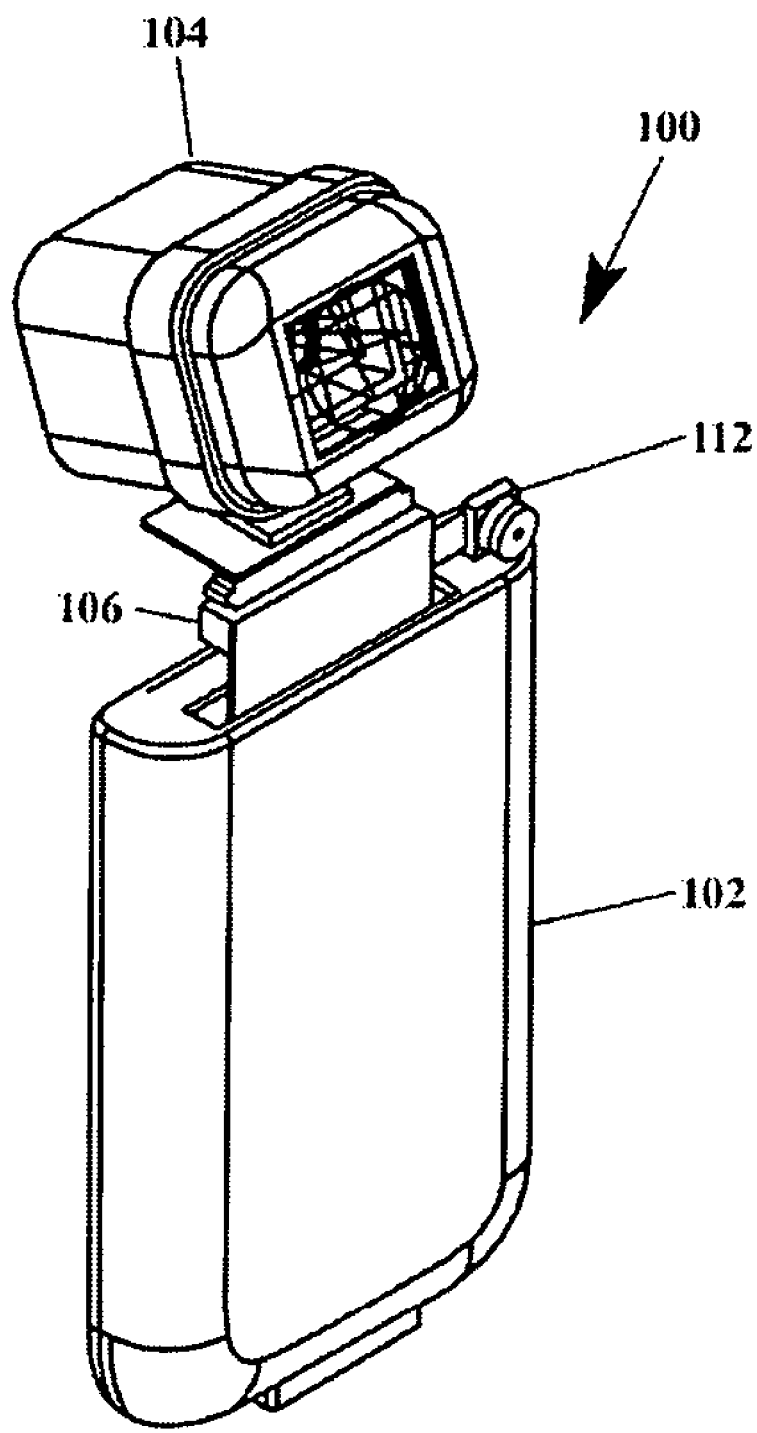
Figure 4:
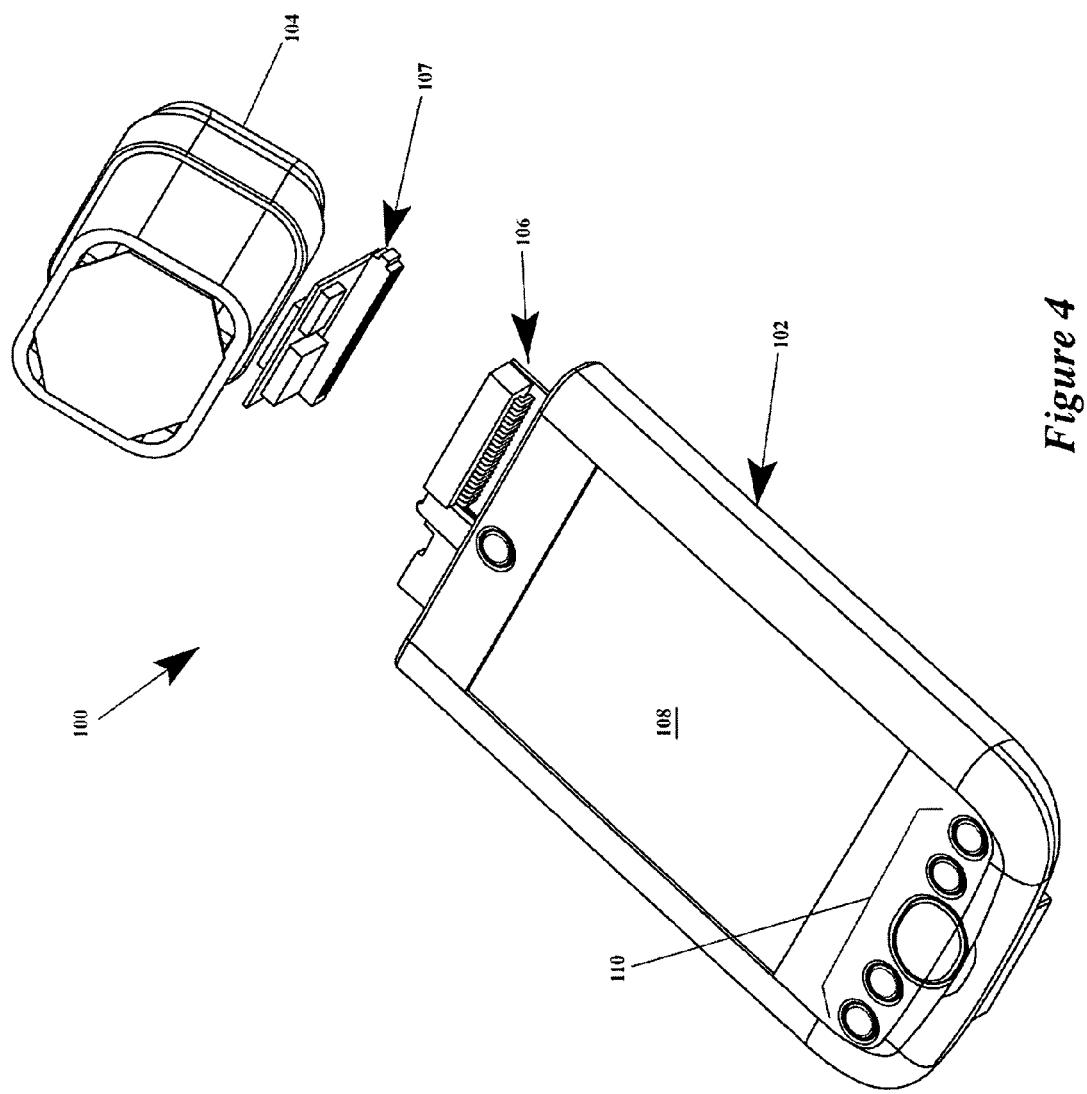
FIG. 4 illustrates a perspective view of one embodiment of the PDA-based imaging system as shown in FIG. 1, with an optics/imaging attachment separated from the PDA to which it connects.
Figure 5:
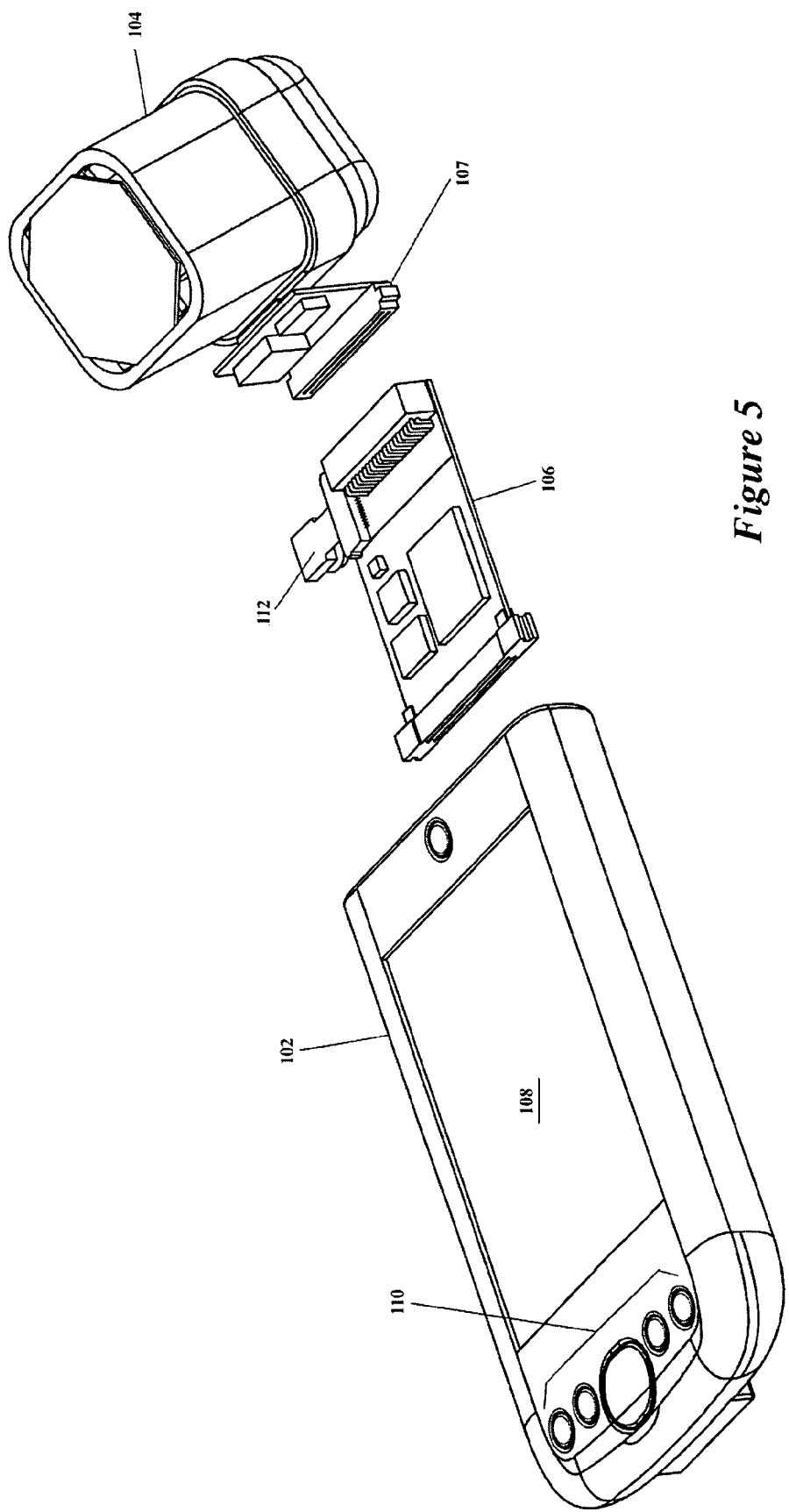
FIG. 5 illustrates a perspective view of one embodiment of a PDA of the PDA-based imaging system as shown in FIG. 4, with a buffer PCBA separated from the PDA and also from the optics/imaging attachment.

As best seen in FIG. 1, the PDA 102 includes a display panel 108, control actuators 110, a flash card slot 1404 (see FIG. 14a, e.g. a compact flash connector), memory 1402 (which may be RAM and/or disk type), and a microprocessor 1406. The PDA 102 is operated by an operating system, such as Windows CE, which in turn manages the application software. The PDA 102 provides user interface functionality and processing power for various software applications stored in the memory 1402. The application software executes on the PDA 102 to present on the display 108 a user interface that utilizes the PDA's control actuators 110 for program control and to send control signals out over the connector 1404, including those signals for the SCCB interface 1470 (see also FIG. 14b) to control image capture at the optics/imaging attachment 104, to receive the image data captured at the image sensor chip 602 and transmitted back over the PCBA 106 and to process the image sensor data. Specifically, the image capture control program for using the SCCB interface 1470 is stored in the PDA memory 1402 and executed on the PDA microprocessor 1406. This control program provides clock signals and data commands per the SCCB interface protocols for control of the image sensor chip 602. The control signals activating the image sensor chip 602 in the optics/imaging attachment 104 originate from control routines implementing the SCCB interface 1470 written in the application software stored in the PDA memory 1402. This software issues commands to capture an image and then receives the stream of image data from the image sensor chip 602 for storage and analysis.

The PDA 102 provides a platform for a user-friendly interface defined in the application software. Providing the control software and all elements of the user interface in the PDA 102 provides not only image display but also an effective control panel for any additional image-related functions needed by users.

PCBA Interface

Figure 14A:
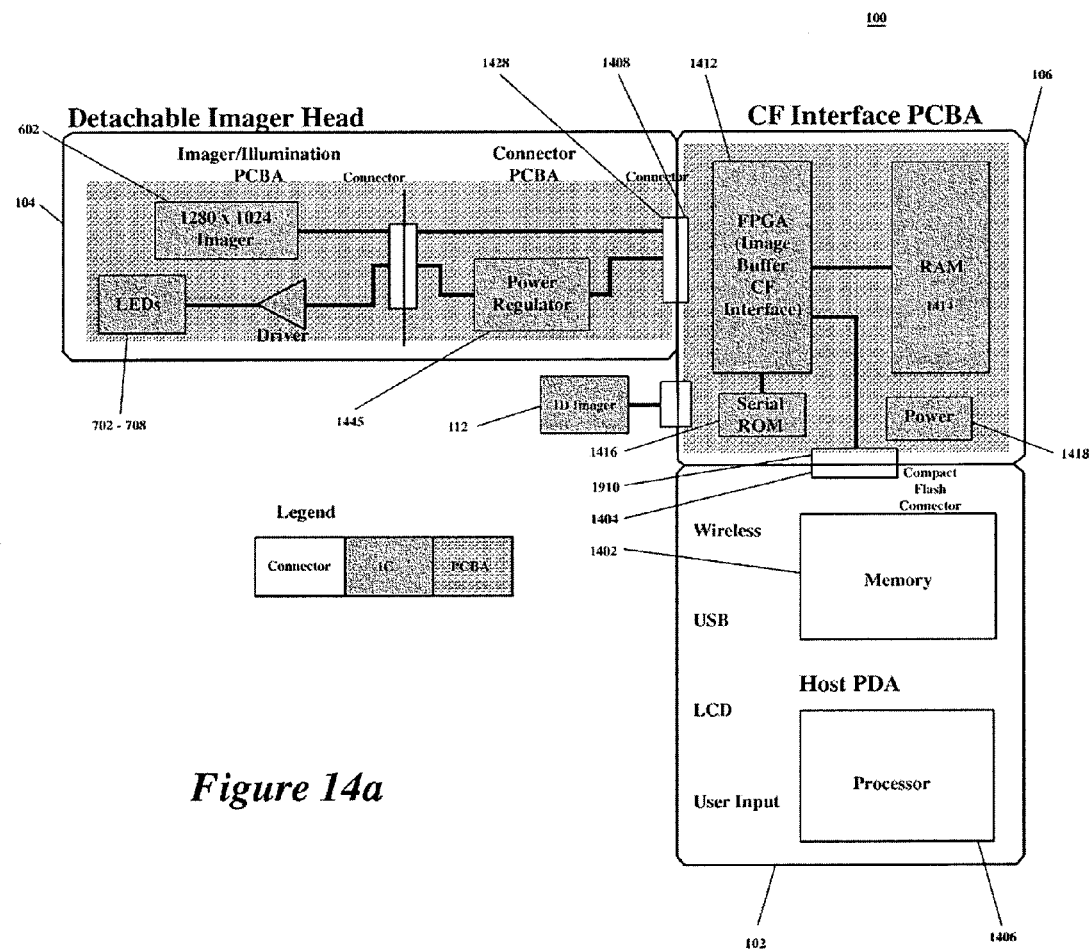
FIG. 14a is a component block diagram of a PDA with a PCBA interface connecting between the PDA and the detachable optics/imaging attachment as shown in FIG. 1.
Figure 14B:
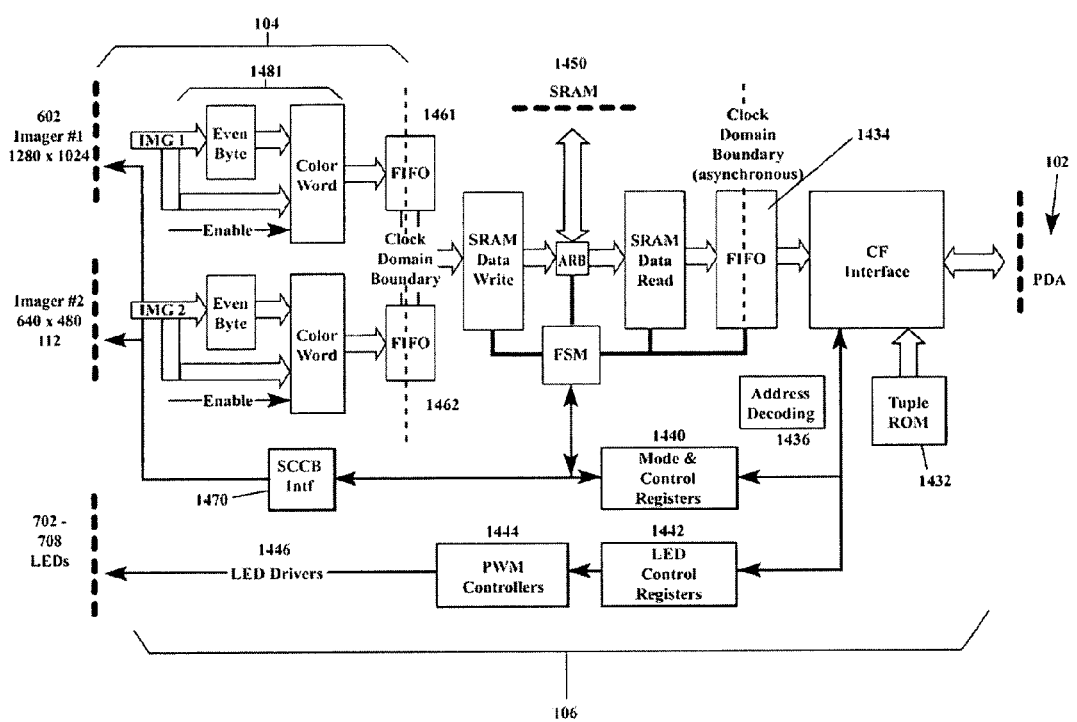
FIG. 14b is a signal flow block diagram corresponding to FIG. 14a for the PDA, PCBA with its face imager and the optics/imaging attachment with its image sensor and LEDs.

As shown in FIGS. 1, 14a and 14b, the PCBA 106 has a first connector 1408 that connects to the optics/imaging attachment 104 on one side and a second connector 1410 that connects to a PDA compact flash I/O connector 1404 on the other side. In one embodiment, the PCBA 106 includes an FPGA (Field-Programmable Gate Array) 1412 with Image Buffer and CF Interface, a RAM 1414, a serial PROM 1416, and a power module 1418 for power filtering and regulation for the components on the PCBA. The PCBA 106 functions to, among other things, queue and forward data from the optics/imaging attachment 104 to the PDA 102. In some instances, specific control signals to the optics-imaging attachment 104 are converted by the FPGA 1412 on the PCBA 106 from signals initiated by the PDA-based application software.

The PCBA 106 also has an additional face image camera 112 that can capture an overall facial image, non-magnified, for display on the PDA screen 108 and storage. For example a Model 7649FSG camera module from OmniVision Technologies, Inc. of Sunnyvale, Calif. may be included as camera 112 on the PCBA 106.

Also part of the PCBA interface is a connector PCBA 107. This portion of the PCBA interface comprises a PC board that is attached to the base of the optics/imaging attachment 104, on which the following components are mounted: Power regulator 1445 and connector 1428. The primary function of this PCBA 107 is physical connection, although it also helps manage power delivered to LED driver 1446 in the optics imaging attachment.

Optics/Imaging Attachment—Control and Output

Turning to FIG. 14*b*, the flow of signals through the FPGA 1412 to and from the PDA 102 and the optics/imaging attachment 104 can be seen. Communication between PDA 102 and PCBA 106 flows across a CF Interface 1430 utilizing the Tuple ROM 1432, which stores identification information for the optics/imaging attachment 106 that is passed to PDA 102. The CF Interface uses Address Decoding module 1436 to exchange data with Mode and Control Registers 1440 and LED Control Registers 1442. The LED Control Registers 1442 send data to the PWM (pulse width modulation) Controllers 1444 that are linked to the LED Drivers 1446 for the LED pairs 702-708.

The Mode & Control Registers 1440 communicate control signals to the SCCB Interface 1470 for each of the face image camera 112 and the image sensor chip 602 of the optics/imaging attachment 104. These control signals cause the face image camera 112 and the image camera chip 602 to capture an image, which is read byte by byte over IMG2 stage 1482 (full face) or IMG1 stage 1481 (magnified image). Data from IMG1 stage 1481 is queued and handled by FIFO buffer circuitry 1461 in the PCBA 106, while data from IMG2 stage 1482 is queued and handled by separate FIFO buffer circuitry 1462. Both FIFO buffers 1461 and 1462 deliver data to the SRAM memory buffer 1450, which when read delivers data from the optics/imaging attachment 104 to a FIFO buffer 1434 connected to the CF Interface 1430 for data delivery to the PDA 102. Mode & Control Registers 1440 also communicate with SRAM memory buffer 1450 to aid in the image data buffering operations.

The optics/imaging attachment 104 may have no switches or buttons or other control elements accessible to a user, so that all control is by signals over the connector interface 1408 of the PCBA 106 to the optics/imaging attachment 104. Alternative embodiments of the control interface may be arranged and configured such that image data is delivered from the image sensor chip 602 directly to the PDA 102. For example, a wireless interface (e.g., based on Bluetooth of similar short-range technology) may be arranged and configured between the image sensor chip 602 and the PDA 102.

The application software, as mentioned above, causes signals as defined by the SCCB interface 1404 to be generated at the flash card slot connections and transmitted (with any necessary conversion) across the PCBA 106 and the Connector PCBA 107 to the SCCB interface 1470 of the image sensor chip 602. The image sensor chip 602 captures images and presents image data back at its outputs, under control of the application software stored on a PDA memory 1402 (see FIG. 14) acting as the SCCB interface "master." In one embodiment, the image sensor chip 602 provides image output data only in response to control signals from the "master."

A benefit of the present invention is that, in one embodiment, changes to control methodology and/or control signals can be readily made via modification of the application software at the PDA 102. Component replacement for changing a control circuit may not be required to update functions or correct errors. A further benefit is that, in one embodiment, with the PDA 102 as the platform, the optics/imaging attachment 104 becomes an interchangeable component. If it is desired to capture hair or other images instead of facial skin images, the optics/imaging attachment can be replaced, and a new control application software on the PDA 102 can be called on to control the operation of the optics/imaging attachment with the new component that captures hair or other desired images.

Software for Image Capture/Processing/Analyzing/Scoring

Figure 15:
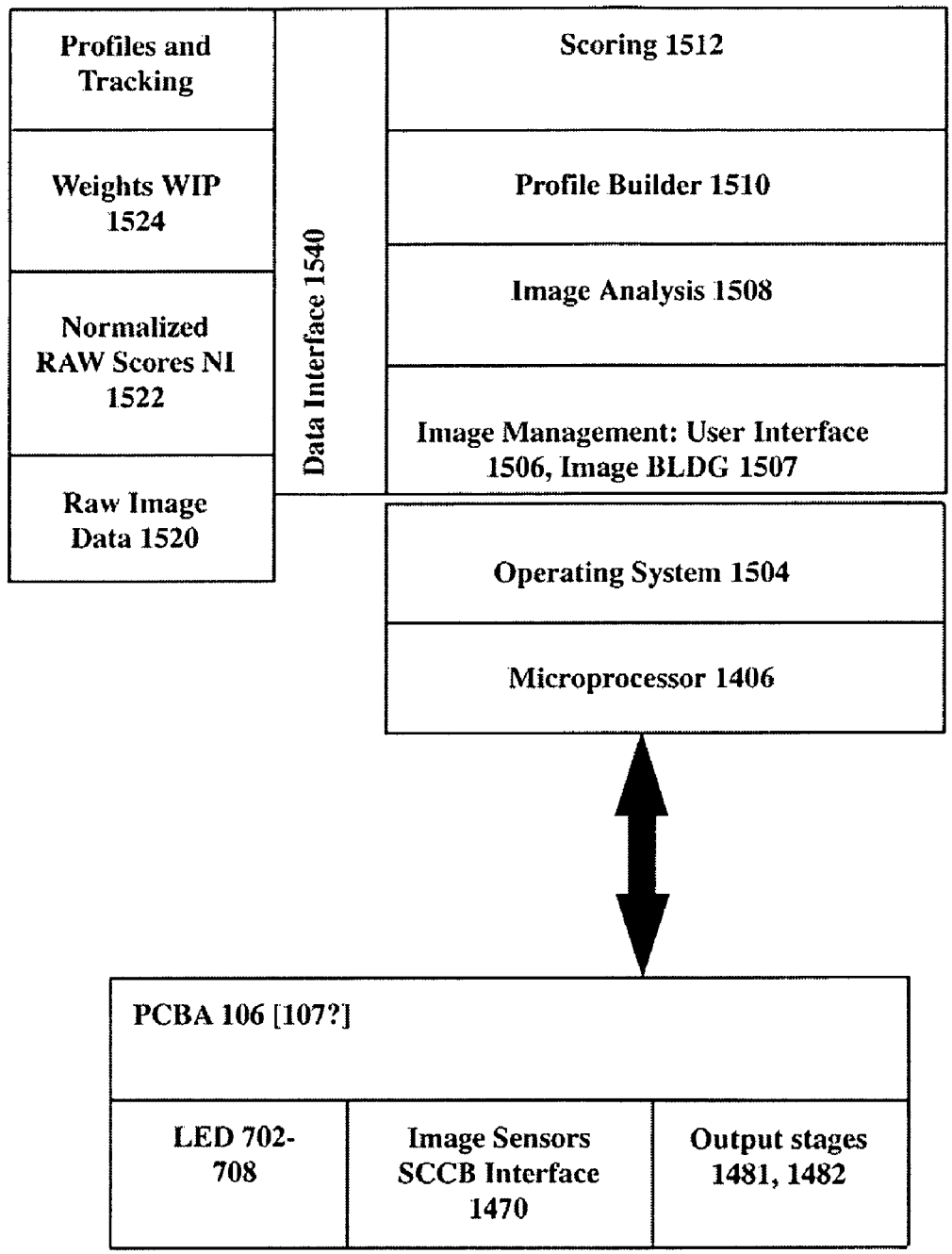
FIG. 15 is a block diagram showing the processor and basic software and data components executing on the processor and used in the invention.

FIG. 15 is a block diagram showing the processor and basic software and data components used in the system. In particular, FIG. 15 shows microprocessor 1406 of a PDA (or other computer platform) on which an operating system 1504 runs. In one embodiment, this is Windows CE, but it may also be an operating system of the Unix or Linux family. Application components that run on this platform to implement the data processing functions of the invention include:

(a) An image management component, including a user interface component 1506, which provides the displays for the operations of image capture, processing, analysis and scoring. This includes display of various operating options and the status of various functions, to provide user control over those operations that require user input or in which the user is given some options for selection. As one function, the user interface provides a user guidance for creating the set of images needed. By presenting a sequence of screens particular to each image needed, the user interface prompts and guides the user through the collection of the specified set of images that provide the raw image data on the condition of the physical attributes of interest. Two examples of screen shots from the user interface are shown in FIG. 21. Specifically, these show screens for entering data for a subject profile that will include the images captured. Similar following screens are used to show each image in the specified set of images used for attribute analysis in a preview and provide an option to save or retake each image.

Figure 16:
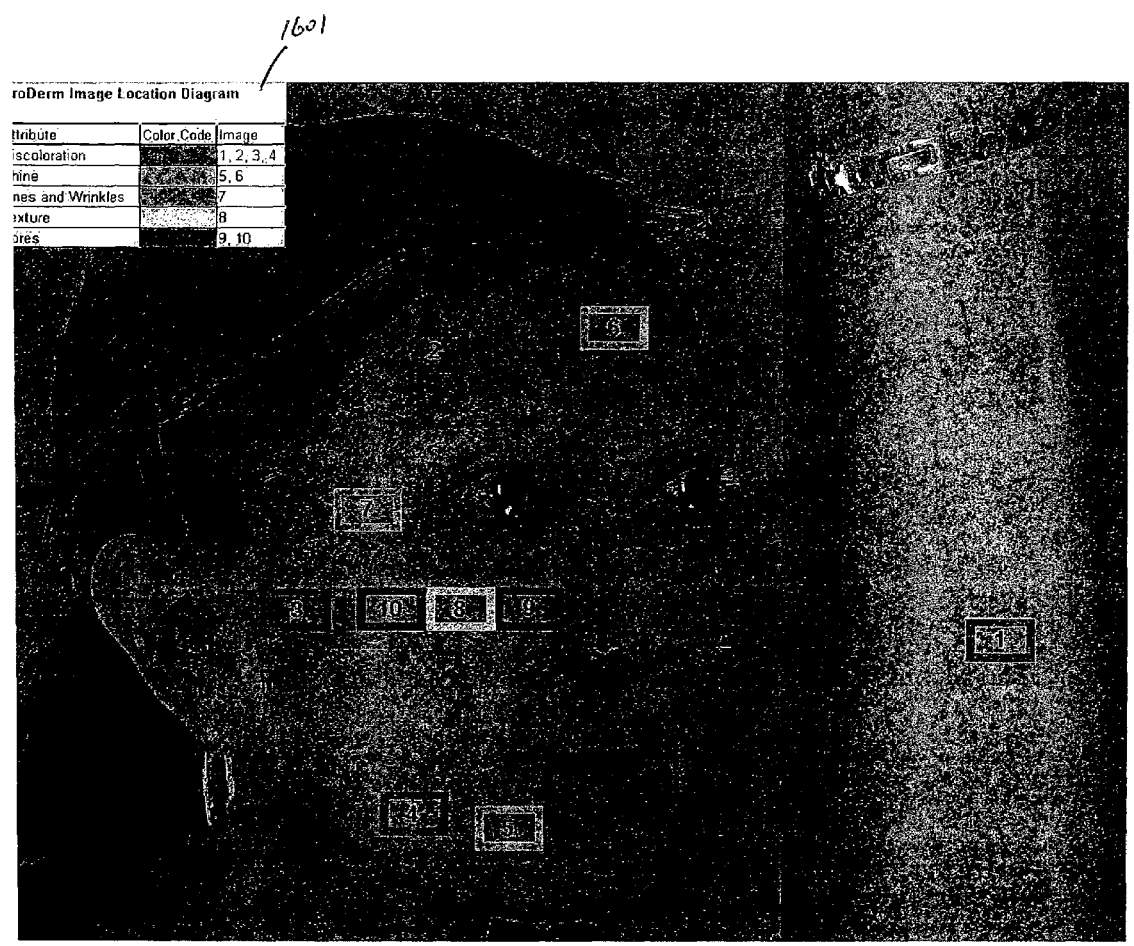
FIG. 16 is a facial photograph marked to show the location of ten different images that are captured in one embodiment of the invention.

For each image, a visual prompt showing the body location or particular view for taking the image is provided. The prompt may, for example, display a portion of the picture of FIG. 16 showing one of the ten numbered areas and "buttons" for taking and saving the image. The prompt for the next image or view is presented to the user only after the user has taken and saved an image as required by each prior prompt. The user interface moves on to image analysis and scoring only after all necessary image data is captured. In one embodiment, the user is prompted to capture at least five images. In another embodiment, the user is prompted to capture ten or more images, with each attribute of interest having a predefined association with at least one of the images captured.

FIG. 16 shows the location on a subject's face and arm of ten different images (identified by the rectangles labeled 1-10) that are captured in one embodiment of the invention designed for skin assessment focused on the face. FIG. 16 also shows in table 1601 five different skin attributes, the condition of which may be assessed using these images (discoloration, shine/oil, lines and wrinkles, texture and pores) and the particular images in that set of ten that will be analyzed to address these attributes. (There might be three, four or more than five attributes of interest and more or less than ten images, depending on the analysis features available and the regimens that might be available to address the skin conditions.) The user interface includes setting up a subject record, stepping through the sequence of image capture with instructions as to where the optics/imaging attachment should be placed, previewing the image before it is finalized, taking the user command for saving or retaking each image in the set and indicating that a saved image set has been passed on for analysis.

Also part of image management, image building component 1507 does collection and initial processing of data from image sensor 602. During the capture of a set of images under direction of the user interface component 1506, the image building component 1507 controls the LEDs 702-708 as needed for the different images taken in a set, i.e., it provides the type of illumination required to each image in the sequence. Thus, when the user interface prompts for each of numbered images 1, 2, 3 or 4 (coloration) per FIG. 16, all LED's will be illuminated and when the user interface prompts for image 7 (lines and wrinkles) only the top LEDs 704 will be illuminated for image capture.

The component 1507 also takes in the image data resulting from a sequence of commands to the SCCB interface 1470 of the optics/imaging attachment 104, and manages delivery and storage of the bytes or other units of image data presented at the output stages 1481, 1482 of the image sensor 602 and the face image camera 112. As needed, the microprocessor 1402 interacts with PCBA 106 to send commands and receive data. The component 1507 then constructs a full pixel image from the data comprising a given "shot," for each of the images prescribed by the user interface sequencing. The component 1507 also can provide warnings and diagnostics on the image collection functions. This can be done by fault detection circuitry that identifies proper/improper function of the LEDs and by basic image monitoring software that can detect severe image defects that might arise with failure of the image sensor 602, or problems in reading the full valid set of image data for any prescribed image.

(b) Image analysis component 1508 is used once a set of pixel images is captured. This raw image data may be processed with pattern recognition and other analytical software to produce for each attribute an annotated image that shows by added lines, boxes or other outlines or markers features of interest for the attribute involved. The analysis component also develops a normalized raw score, rating the observed condition of the subject's skin for each attribute of interest. This score can be based on a variety of evaluation algorithms developed to quantify the attribute. Generally, the goal is to have the software represent the judgment of a dermatologist or similar expert professional relative to the particular subject. This helps avoid the biases that may arise in a system that does a comparative analysis based on the statistical variations found in a particular population.

In one embodiment, for software development, a software programmer's algorithms first delineate the features of the skin for a number of subjects. This basic image processing for feature recognition may be done with use of a variety of public domain image analysis algorithms addressing: grayscale thresholding, contour detection, color coding, deviation, Gaussian smoothing, line tracking, mean and variance of the feature points, etc. (See: *Digital Image Processing* (2$^{nd}$ *Edition*), Gonzalez and Woods, Prentice Hall, @ 2002; *Introduction to Computer Graphics*, by Foley, Van Dam, Feiner, Hughes, and Phillips, Addison-Wesley Publishing; see also: for Gaussian smoothing filter: http://homepages.inf.ed.ac.uk/rbf/HIPR2/gsmooth.htm; for average smoothing filter: http://www.incx.nec.co.jp/imap-vision/library/wouter/avef5gaus.html; for linear smoothing filter: http://www.ph.tn.tudelft.nl/Courses/FIP/noframes/fip-Smoothin.html; for image feature line detection methods by derivative-based operations: http://www.ph.tn.tudelft.nl/Courses/FIP/noframes/fip-Derivati.html; by Laplacian filter: http://www.dai.ed.ac.uk/HIPR2/log.htm: http://www.websupergoo.com/helpie/source/2-effects/laplacian.htm; http://www.opengl.org/resources/tutorials/advanced/advanced97/notes/node171.html; for image feature lines (for texture and wrinkles): http://www.reindeergraphics.com/tutorial/chap6/binary09.html; for correlation and feature detection: http://www.opengl.org/resources/tutorials/sig99/advanced99/notes/node261.html; for image histogram: http://www.cambridgeincolour.com/tutorials/histograms1.htm; http://deming.eng.clemson.edu/pub/tutorials/qctools/histm-.htm; http://www.luminous-landscape.com/tutorials/understanding-series/understanding-histograms.shtml; for image thresholding: http://www.reindeergraphics.com/tutorial/chap5/thresh01.html; http://www.pages.drexel.edu/~weg22/hist thresh cent.html; for statistics mean and variance: http://www.stats-consult.com/tutorial-04/tutorial-04.htm.) Images taken with the device are annotated by an expert dermatologist and the features the expert finds significant are targeted by the software developer for further algorithm adjustment or refinement to identify and scale that attribute, in a sense, duplicating the dermatologist's eyes in identifying, differentiating and rating the attributes of interest.

For more quantitative analysis, a dermatologist expert collects clinical study subjects into groups that have poor (−), average (0) and excellent (+) ratings for each of the 5 attributes that the device measures, i.e., Lines and wrinkles (L&W), Texture, Coloration, Pores and Oil. The dermatologist then uses the device on the clinical study subjects to image the areas designated for the evaluation set and the software generates its raw score data for each attribute. The values are then sent along with the images to a software programmer who adjusts the algorithms so that the software can duplicate the {−, 0, +} assignments made by the dermatologist. Finer numerical ratings may be developed in somewhat the same way, with collections of clinical images ordered by a dermatologist's numerical rating (instead of the {−,0,+}ratings) and some interpolation. This way, the judgment of the expert dermatologist is placed into the analysis software 1508.

The result of processing by the analysis software 1508 is that analysis software 1508 will deliver a set of raw scores computationally derived from those images in a set of images for a subject that are considered relevant to an attribute, e.g., referring to table 1601 of FIG. 16, the "coloration" raw score will be derived from images 1, 2, 3 and 4, "shine" raw score will be derived from images 5 and 6, etc. One raw score per attribute is provided, but more could be produced if more than one analytical measure were used for the attribute. Normalization of the subject's raw scores may be built into the analysis software, because is desirable to place all attributes scored on the same rating scale. The set of raw scores may be used to help a subject understand whether the observed conditions are, in the eyes of a dermatologist, normal or above or below normal and by how much; however, as discussed below, these scores are more useful for product selection after further processing.

Figure 22:
FIG. 22 shows a report developed for a particular subject with scoring scales.

(c) A profile builder component 1510 assembles the images and set of normalized raw scores for each skin attribute into a preliminary profile that is ready for further, product-based scoring. If the raw scores are presented, a profile screen as in FIG. 22 with a set of bar graphs for the attributes of interests may be used. The profile may combine data from the magnified pixel images with a full facial image, as shown in FIG. 22.

(d) A scoring component 1512 is designed to help connect the objective results of the analysis software 1508 with the product regimens available for addressing various skin problems. This is done because the images captured are selected to provide information on three or more and, in one embodiment, five, skin attributes. The information available on skin attributes is multidimensional. Further, each regimen may have different value for treatment of each of the multiple attribute dimensions that are evaluated from the captured image. Thus, for purposes of regimen selection, it is often appropriate to give greater weight to those attributes (or dimensions) that are most in need of improvement and most susceptible to improvement given the available products. Also, if a particular regimen will be used for a period of time, it is useful to have a baseline score that is based on that regimen to use for tracking improvements. The scoring system thus plays a dual role. On the one hand, it reports from a product regimen viewpoint on the condition of the attributes of interest as observed in captured images. On the other hand, it is used to help select a product regimen recommendation that addresses the condition of the attributes of interest as observed in captured images and may also take into account subjective data not shown in the images, such as age, or recent changes in skin condition.

Referring again to FIG. 15, the applications 1506, 1507, 1508, 1510 and 1512 use a data interface 1540 to access and modify files containing Raw image data 1520, Normalized Scores 1522, Weights 1524 and Profile and Tracking Data 1526. The Profile and Tracking Data 1526 may be useful for assisting a user and subject in storing data that reveals the effect of treatments. The user may repeat the image capture sequence at various times after use of a product regimen begins and build a date-labeled file of the resulting scores over time.

Scoring and Product Selection Procedures

FIG. 18 shows several attributes of a product-based scoring system. At the top of FIG. 18 is a depiction of a numerical point scale from zero to 1000 that may be used in one embodiment to rate the measured condition of all attributes, derived from a set of images and related data. (The range is largely arbitrary and could also be 0-500, 0-100, 0-10 or 1-7, as long as it is sufficiently fine-grained to distinguish among bad, average and excellent status of the attributes of interest and allows measuring improvement in the attributes over time.) Raw scores from analysis are normalized to the selected range of values. Below that point scale is a table that shows sample normalized raw scores Ni for each of the attributes (i.e., N1, N2, N3, N4, N5, a five element score vector, when there are five attributes (i) of interest). Here N1 (L&W)=650, N2 (texture)=500, etc.

Because the scoring approach is product based, the number of available products involved in scoring plays a role. The scoring system to be described is useful primarily when there are three or more different product regimens. Although not necessarily used in scoring, a product recommendation may also include products ancillary to a product regimen that address a particular condition or mix of conditions. An example using five attributes of interest and five scoring regimens (with ancillary products) will be used to illustrate how scoring proceeds.

Weights

A preliminary step in the product-based scoring system is to define a set of weights Wip, one for each of the attributes (i) and for each of the treatment products or regimens (p). In FIG. 18, the "Scoring Weighting" table immediately below the example raw scores is a matrix with a cell for each of five product regimens (180™, TPW™, CA™, Nutricentials C/O™, and Nutricentials C/O™) and each of the five attributes of interest. The weight defining process begins by assigning for a given product regimen a rating from zero to 100 as to each of the attributes, based on the product regimen's ability to improve the attribute, if it is found deficient in a subject. For example, the "180™" regimen is viewed as very helpful for lines and wrinkles and for texture (ratings=100) but not measurably helpful for coloration, pores or oil (ratings=0), and the "TPW™" regimen is viewed as very helpful for texture and for coloration (ratings=100), somewhat helpful for pores (rating=20), but not measurably helpful for lines and wrinkles or oil (ratings=0). The "CA™" regimen is viewed as not measurably helpful for lines and wrinkles (rating=0), very helpful for texture (rating=90), moderately helpful for coloration and pores (ratings=40), and somewhat helpful for oil (rating=20). The Scoring Weighting table continues with ratings for the "Nutri C/O" and Nutri N/D" product regimens. In addition to the individual attribute rating on the scale from zero to 100 for each product regimen, in the rightmost column the table also shows a total of the individual attribute ratings for the product regimen, e.g., "180™" total=200, "TPW™" total=220, etc.

The "Scoring Weighting as a %" table that appears below the "Scoring Weighting" table shows the calculated percent contribution of the individual attribute ratings to the total of ratings for each product regimen, using the values for each product regimen shown in the "Scoring Weighting" table and the total shown in the rightmost column of the "Scoring Weighting" table. This results in a matrix of percentage-based weights Wip.

The "Scoring" table that appears below the "Scoring Weighting as a %" table then shows how the percentage weights Wip calculated for each attribute and for each product regimen are applied as weights to the sample raw score set or vector {600, 500, 450, 450, 500} to produce adjusted normalized scores. Thus, for the product regimen "180™", the lines and wrinkles raw score of 650 is multiplied times 50% (the weighting Wip for that attribute relative to the "180™" product) to yield an adjusted normalized score ANip of 325 for lines and wrinkle and the "180™" product, and the texture raw score of 500 is multiplied times 50% (the weighting Wip for that attribute relative to the "180™" product) to yield an adjusted normalized score ANip of 250 for texture and the "180™" product. The other attribute raw scores are multiplied times 0% (the weighting Wip for those attributes relative to "180") and yield zero values for coloration, pores and oil for the "180™" product regimen. Similar calculations are done to produce adjusted normalized scores ANip from the individual attribute raw scores for each of the attributes relative to each of the other product regimens, TPW™, CA™, NutriC/O™ and Nutri N/D™. The adjusted normalized scores ANip for each of the attributes are added to provide a total adjusted normalized score TANp for each of the product regimens (p).

The total adjusted normalized scores TANp for each product regimen may be output and presented as results for the subject and to provide a basis for a product regimen to be recommended. However, they are more usually saved for a later step in the product recommendation process.

Product Recommendation Association Table

A second set-up step for product recommendation is defining an association between scores and products; that is, for each score set (in our example the raw score vector or quintuple {N1, N2, N3, N4, N5, where Ni is an integer}) an association with one product regimen is defined. This association may be represented in various ways known to those skilled in the art. In one embodiment, this is done in a table as in FIG. 19. While a table based on raw scores and possible combinations/vectors of these is possible, to reduce complexity that would result from having a separate product recommendation for each theoretically possible raw score quintuple ($1000^5$ possibilities with a 0-1000 raw scoring scale), a starting point for this table is that each normalized raw score value is mapped into a code for a level in a simplified range consisting of three or more levels (typically, no more than ten or no more than seven levels). In one embodiment (shown in FIG. 15) there are three levels for each attribute: (a) "poor" symbolized by "−" and corresponding to a Ni value in the range zero to 400; (b) "average" symbolized by "0" and corresponding to a Ni value in the range 401 to 600; and "Excellent" symbolized by "+" and corresponding to a Ni value in the range 601 to 1000. (Other mappings with more levels are possible, e.g., the above mapping but with "poor" corresponding to a range 201-400 and "very poor" corresponding to a range zero-200 This three-level mapping permits each quintuple of normalized raw scores {N1, N2, N3, N4, N5} to be mapped into a simplified condition quintuple {C1, C2, C3, C4, C5}, with each Ci being "−", "0" or "+". This reduces the possible combinations to no more than $3^5$ possibilities or 243.

Next, a table as shown in FIG. 19 is generated, enumerating a plurality of the possible simplified condition quintuple combinations. Some combinations not expected to occur may be omitted. Typically, a substantial portion, or a majority of, or all possible simplified quintuple combinations {C1, C2, C3, C4, C5} that might appear in a large population of subjects for whom normalized raw scores are developed and translated into a quintuple will be placed in the table. (The possible combinations are enumerated by the numbers 1 through 243 in the first column 1901 of FIG. 19, while the specific values of the Ci in each quintuple appear at the third through seventh columns of FIG. 19.) For each quintuple combination {C1, C2, C3, C4, C5}, a product expert selects a recommended product regime that is then identified in the second column of FIG. 19. If the expert decides that an additional, ancillary product would be useful with those that are part of the selected product regimen, that is inserted into an eighth column of FIG. 19.

As can be seen, with any raw score quintuple {N1, N2, N3, N4, N5, where Ni is an integer} the scoring system as shown in FIG. 18 can map to a simplified condition quintuple {C1, C2, C3, C4, C5}, with each Ci being "−", "0" or "+", and the table of FIG. 19 can lead to a product recommendation. However, a product recommendation need not be driven entirely by raw scores derived from image data, and in one embodiment, the system prompts for and receives at least one item of data that is separate from the data derived from images. In one embodiment, that separate piece of data is a subjective report, based on self-reported information. It may also be data reported by an observer of the subject or developed by another measuring tool.

Figure 20:
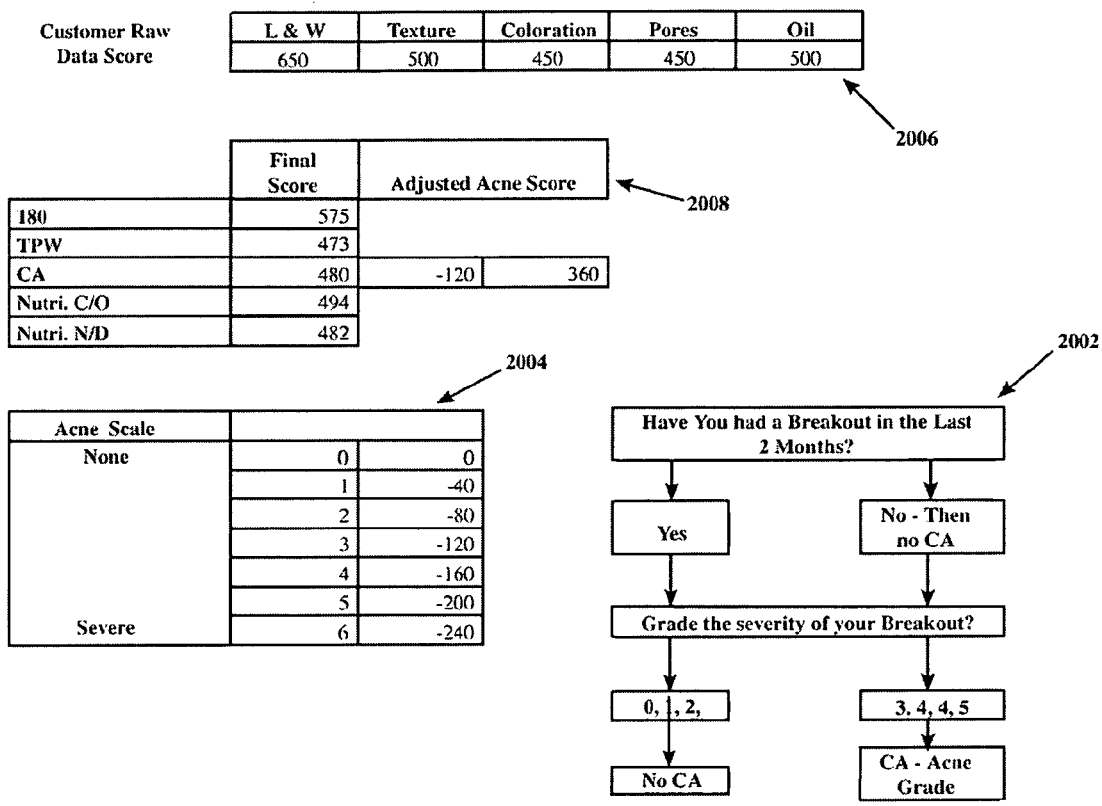
FIG. 20 is a set of tables and a flowchart showing a logic path for scoring and selection associated with the CA™ product.

Referring now to FIG. 20, the flowchart 2002 in the lower right-hand corner shows a sample subjective inquiry, in this example to obtain self-reported information on the history of acne breakouts that would not be fully visible in the images collected. The subject is asked about the occurrences of any breakouts in some specified time period. If the subject reports none, then the acne specific product "CA™" regimen need not be considered and product recommendation can be based on FIG. 19 associations. If the subject reports that there has been a breakout in the relevant period, then the subject is asked to grade the severity on a scale of zero (negligible) to 6 (severe). If the ranking is in the range 0-2, then acne specific product regimen "CA" need not be considered, and product recommendation again can be based on FIG. 19 associations.

If the ranking is in the range 3-6, then acne specific product regimen "CA" is recommended. To set up a product-based scoring baseline for a subject that receives this recommendation, the scoring and product selection logic returns to the total adjusted normalized score TANp. As shown in the lower left-hand portion of FIG. 20, there is a table 2004 defining an Acne Scale that maps each of the self-reported breakout severity levels to a scoring adjustment. All values are negative, because all are indicative of a self-reported unfavorable historical condition that is not accounted for (or not fully accounted for) in the normalized raw scores 2006 from images or any numbers derived from them by product regimen weighting. The more severe the self-reported breakout, the greater the downward adjustment. In the adjustment example shown in the table 2008 just above the Acne Scale table, it is assumed a severity level of "3" was self-reported and an adjustment of (minus 120) is applied to the total adjusted normalized score for the product CA (TANca), reducing the original adjusted normalized score for CA from 480 to 360. Thus, the person starts the recommended CA product regimen with a baseline that reflects more data than was discernible from the image data alone.

If the CA product regimen is not selected as a result of the additional sample subjective inquiry (in the example, directed to acne, but the inquiry could also be about age, sun exposure or any other relevant factor a subject might report or a skin professional might observe and report), then the scoring and product recommendation module returns to the table of FIG. 19 and from the simplified condition quintuple {C1, C2, C3, C4, C5}, derived from the subject's images and normalized raw scores, the scoring software finds a product regimen recommendation. This is provided as output.

The logic shown in FIG. 20 may, alternatively, in part be implemented in a supplement to a table and in FIG. 19. In the case where a particular data item is considered determinative for product selection, that data item can have its own column in FIG. 19 alongside the other Ci columns. For example, FIG. 19 could have a column expressing logic applied to self-reported data on acne breakout severity. The logic associated with the column is that if the reported severity if 3 or higher, then the associated product recommendation is CA™ without regard to any value {C1, C2, C3, C4, C5} otherwise determined for the subject. The further logic is that if the reported severity is less than 3, then the reported value is not used in product selection and the other Ci values are used for determining a product recommendation.

Figure 17:
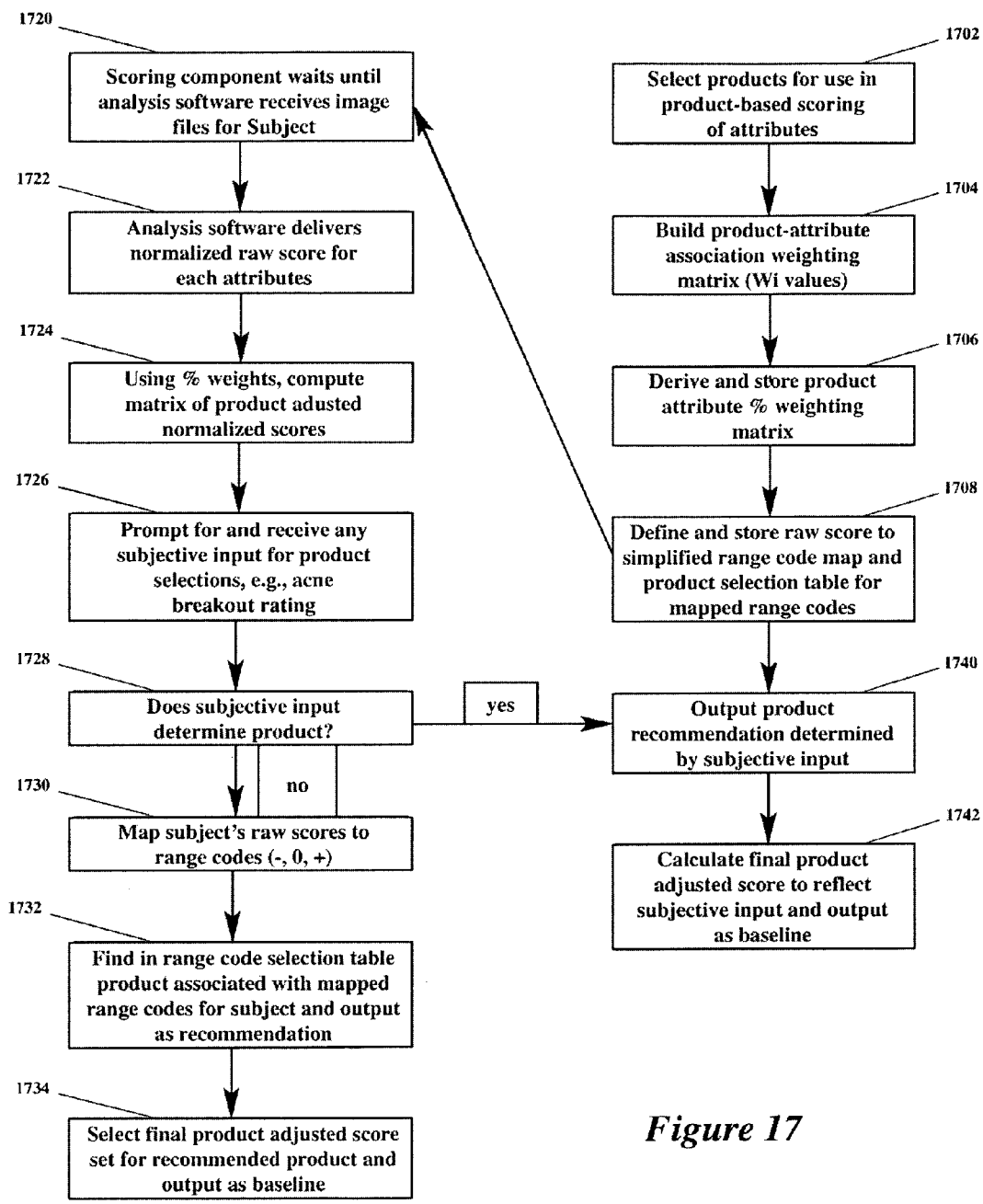
FIG. 17 is a flow diagram of an exemplary process for processing/analyzing/scoring captured image data and related data in application software in accordance with the principles of the present invention.

FIG. 17 summarizes and depicts in flowchart form, the steps of the product based scoring method. To begin the method, the application user selects the product regimens for use in scoring for the attributes of interest 1702. Then a product attribute weighting matrix is built 1704 as in FIG. 18. The user then derives and stores the product attribute weights, i.e., the values Wi shown in FIG. 18. To set up a chart as in FIG. 19, the user then defines and stores a raw score to simplified range code map and builds the product selection table 1708 for at least a substantial portion of the possible combinations of range codes, i.e., the possible quintuples of values {C1, C2, C3, C4, C5}. The scoring component waits until the image analysis software receives image files for a subject 1720. Then, with that data available, the analysis software delivers a normalized raw score for each attribute 1722. Using % weights, the application computes a matrix of product adjusted normalized scores 1724, which may be displayed or simply stored pending further progress in the scoring logic. The application will then prompt for and receive any subjective input for product selection, e.g., acne breakout rating 1726. A decision point is reached: Does subjective input determine the product regimen to be recommended? 1728. (Depending on the implementation, this will be implemented in a separate logic piece or be built into the table of FIG. 19a-19e.) If the decision answer is "yes", then the application outputs the product regimen recommendation determined by the subjective input 1740. To complete this logic branch, the application calculates a final product adjusted score to reflect the subjective input and to output as a baseline 1742.

If the decision answer is "no", then the application maps a subject's raw scores to range codes (−, 0, +) 1730, in preparation for use of the table of FIG. 19. With the mapped quintuple {C1, C2, C3, C4, C5} for the subject, the application finds in the range code selection table a product regimen associated with the specific mapped range codes for the subject and outputs this as a product regimen recommendation 1732. To complete this logic branch, the application now selects a final product adjusted score set ANip that corresponds to the recommended product regimen and outputs that as a baseline 1734.

Alternative Applications

The above discussion of a system for skin analysis focused on the face uses an expert system that is supplied data from analytical measurement (the capture of color pixel images and the evaluation of patterns within that image) and certain human input (expert user or customer subjective self-assessment). But the system and method described may also use data supplied from analyses other than image based and may provide analysis of conditions in the hair, or particular body locations other than the face, or particular locations where a condition such as psoriasis is present. Here image data may be part of the relevant data but other data may be required as well. For example, a user may enter via the PDA user interface the pH of the subject's skin measured with a separate instrument. Or the subject may provide material for a biochemical assay for a unique skin, hair, sweat, blood, saliva molecule. The resulting assay value may be entered into the PDA user interface to derive the state of health of the skin with special conditions, hair, organism, etc. and/or to allow the accurate recommendation of certain products that address conditions measured.

The removable optics/imaging attachment 104 allows changes in the data collected and delivered to the applications running on the PDA. The standard interface to the PDA used by the optics/imaging attachment 104 permits the possible use of other, image or non-image based, analytical measurements for use in recommending hair care products, recommending specific skin care treatments or to assess the overall health of an individual.

In the case of hair, image analysis would remain important but would use a different optics/imaging attachment 104. Here the user interface would guide the user to collect image data showing several strands of hair using higher magnification. (It is necessary to see the cuticle of the hair, scale-like structures on the surface of the hair shaft). The lighting in the optics/imaging attachment 104 adapted for hair may be more intense and directed at an angle differing from that used for skin. The light delivered on the object plane may include polarization. By selection of other LEDs, the illumination may use specific wavelengths to produce sufficient detail of the cuticle. The illumination parameters are selected so that the software analyzing the images may measure the angle of the cuticle away from the shaft, the number of regular vs. irregular cuticle plates, and other attributes reflecting the condition of hair.

In one embodiment, the user interface may guide the user to obtain several strands of hair removed from the head and placed on a standardized surface for imaging. If the optics/imaging attachment 104 is used directly on the head, in situ, an outline function may be included in the user interface and an image generating procedure to allow the designation of several hair shafts in the gross image. With hair the system is focused on a different set of attributes, for example, three of more of: shine, cuticle size, angle at which the cuticle is lifted from the hair shaft, hair diameter, coloration, splitting. These attributes may be selected based on products available to address them, such as products addressing subjects with damaged hair, thin hair, dull hair, etc.

The scoring methodology above may be related to these attributes of hair, and weights reflecting the affect of available product regimens on specific hair attributes may formulated. Further, with scores available rating the condition of the attributes for a subject, a product recommendation table may be built using the same approach of defining a vector with multiple elements corresponding to the hair attributes of interest and the products suited to the possible combinations of attributes that may appear in subjects. Similar to the table of FIG. 19, a table can be built associating the possible vectors with multiple elements corresponding to the hair attributes with hair care products recommended for subjects with specific multidimensional conditions defined by the vectors.

The system and methods described above may be used for skin conditions other than those found on the face. The attributes of lines/wrinkles, texture, pores, coloration and shine are also relevant to dryness on the feet or hands or to highly discolored areas anywhere on the body. An analysis of these other skin areas may be done with the same optics/imaging attachment 104 but with software that evaluates and scores the resulting data differently. The same general evaluation and scoring described above can be adapted to direct the user to the appropriate products to reduce dryness in the affected skin area or to use of a preventive treatment addressing coloration of a non-face area, such as use of sunscreens.

The above system and method are also applicable to image capture for medical applications. The optics/imaging attachment 104 may be used to capture images of moles, with sufficient detail of the border, and disclosing the blood vessel pattern within the skin, along with the texture and line/wrinkle (surface topography). Such images can provide a clinician a valuable tool in assessing skin lesions and documenting specific areas of skin for later follow-up. The above scoring methods may also be adapted to guide a medical professional in the selection of prescription or non-prescription medicines that are known to address the conditions that may be revealed by images of medical conditions. Here, a medical professional may define the weights and conditions to product associations used in the above scoring and product recommendation methodology. The above system and method may be adapted to guide the medical user through a collection of best practices for image collection and the tables associating multidimensional conditions with product recommendations may embody medical best practices for treatment regimens.

From the above description and drawings, it will be understood by those of ordinary skill in the art that the particular embodiments shown and described are for purposes of illustration only and are not intended to limit the scope of the present invention. Those of ordinary skill in the art will recognize that the present invention may be embodied in other specific forms without departing from its spirit or essential characteristics. References to details of particular embodiments are not intended to limit the scope of the invention.

What is claimed is:

1. An illumination system for use in capturing digital images of body features, where the images represent a plurality of views selected to reveal a condition of three or more attributes of those features, comprising:
   a first light source;
   a light baffle for receiving at an entry of a first channel light flux from the first light source;
   a first reflector element associated with the first channel for receiving light from the first light source and redirecting it to the plane of an imaging station at a grazing angle of ten to thirty degrees;
   a second light source, the light baffle receiving at an entry of a second channel the light flux from the second light source; and
   a second reflector element associated with the second channel for receiving light from the second light source and redirecting to the plane of the imaging station at a grazing angle of ten to thirty degrees; wherein
   the first light source, light baffle and first reflector element are configured so that the imaging station receives from the first light source substantially only a flux of light that has been reflected by the first reflector element; and wherein
   the second light source, light baffle and second reflector element are configured so that the imaging station receives from the second light source substantially only a flux of light that has been reflected by the second reflector element.

2. The illumination system of claim 1, wherein the first and second light sources and their corresponding first and second reflector elements are configured such that when the vector of their respective light fluxes is projected onto the plane of the imaging station, the respective light fluxes intersect at an angle of approximately ninety degrees.

3. The illumination system of claim 1, wherein the first and second light sources and their corresponding first and second reflector elements are configured such that when the vector of their respective light fluxes is projected onto the plane of the imaging station, the respective light fluxes are approximately parallel but have opposed directions.

4. The illumination system of claim 1, further comprising:
   a third light source, the light baffle receiving at an entry of a third channel the light flux from the third light source;
   a third reflector element associated with the third channel for receiving light from the third light source and redirecting it to the plane of the imaging station at a grazing angle of ten to thirty degrees; and
   wherein the third light source, light baffle and third reflector element are configured so that the imaging station receives from the third light source substantially only a flux of light that has been reflected by the third reflector element.

5. The illumination system of claim 4, further comprising:
   a fourth light source, the light baffle receiving at an entry of a fourth channel the light flux from the fourth light source;
   a fourth reflector element associated with the fourth channel for receiving light from the fourth light source and redirecting it to the plane of the imaging station at a grazing angle of ten to thirty degrees; and
   wherein the fourth light source, light baffle and fourth reflector element are configured so that the imaging station receives from the fourth light source substantially only a flux of light that has been reflected by the fourth reflector element.

6. The illumination system of claim 5, wherein the third and fourth light sources and their corresponding reflector elements are configured such that when the vector of their respective light fluxes is projected onto the plane of the imaging station, the respective light fluxes intersect at an angle of approximately ninety degrees and the flux of one of the third light or fourth light sources relative to the flux of the first light source, when the vector of their respective light fluxes is projected onto the plane of the imaging station, is approximately parallel but has an opposed direction.

7. The illumination system of claim 5, wherein the first and second light sources and their corresponding reflector elements are configured such that when the vector of their respective light fluxes is projected onto the plane of the imaging station, the respective light fluxes are approximately parallel but have opposed directions and the flux of one of the third light or fourth light sources relative to the flux of the first light source, when the vector of their respective light fluxes is projected onto the plane of the imaging station, is approximately orthogonal.

8. The illumination system of claim 5 further comprising a controller configured to selectively illuminate the imaging station using one or more of the first though fourth light sources.

9. The illumination system of claim 5 further comprising a controller configured to selectively illuminate the imaging station using one of the first through fourth light sources, with the light source selected to deliver light that is generally orthogonal to the longitudinal dimension of lines or wrinkles to be imaged.

10. The illumination system of claim 5 wherein at least one light source comprises at least one LED emitting substantially white visible light.

11. The illumination system of claim 5 wherein each light source comprises at least one LED emitting substantially white visible light.

12. The illumination system of claim 5 wherein at least one reflector element is a mirror.

13. The illumination system of claim 5 wherein at least one reflector element is a prism.

14. The illumination system of claim 1 wherein the light baffle surrounds an optical system for receiving light reflected from a body surface area located at the imaging station.

15. The illumination system of claim 5 further comprising means for receiving from a control program for the illumination system that controls capture of a specified sequence of images signals that selectively illuminate one or more of the first through fourth light sources to provide a first illumination configuration for at least one image in the sequence of images and a second illumination configuration for at least one other image in the sequence of images.

16. The illumination system of claim 1 wherein the body features relate to skin and the three or more attributes are selected from the group consisting of:
   discoloration, oil/shine, lines and wrinkles, texture and pores.

17. The system of claim 1 wherein the body features relate to skin and the attributes of the body features are: discoloration, oil/shine, lines and wrinkles, texture and pores.

18. The illumination system of claim 1, further comprising a base unit with a processor and a display.

19. The illumination system of claim 18, further comprising an image management software component for presenting on the display a user interface to prompt a user to capture images in preselected locations on a body and to receive captured image data.

20. The illumination system of claim 19, wherein the first and second light sources are under the control of the user interface.

21. The illumination system of claim 20, wherein the first and second light sources provide light following first and second light paths, which when projected onto the plane of the imaging station, intersect at an angle of at least sixty degrees.

22. The illumination system of claim 21, further comprising an image sensor for receiving light from the light sources that is reflected from the surface of a body feature located at the imaging station and for producing pixel image data representing the body feature.

23. The illumination system of claim 22, further comprising a rating software component receiving the pixel image data from the image sensor and configured to mimic the judgment of a dermatologist to provide a rating vector from a set of possible rating vectors representing the condition of three or more attributes of the body feature represented by the pixel image data.

24. The system of claim 23 further comprising a scoring software component for associating one or more of the possible rating vectors with a product regimen for treatment of the condition of at least one of the three or more attributes of the body feature represented by the pixel image data.

25. The system of claim 1 wherein the light sources are LEDs.

26. The system of claim 19 wherein the user interface has controls for selectively illuminating one or both of the first and second light sources to produce pixel image data.

27. The system of claim 23 wherein the body feature located at the imaging station is skin and the three or more attributes of the body feature are selected from the group consisting of: discoloration, oil/shine, lines and wrinkles, texture and pores.

28. The system of claim 23 wherein the body feature located at the imaging station is skin and the attributes of the body feature are: discoloration, oil/shine, lines and wrinkles, texture and pores.

29. The system of claim 1 wherein the first and second light sources provide light following first and second light paths that when projected onto the imaging station intersect at an angle of ninety degrees.

30. The system of claim 1 wherein the first and second light sources provide light following first and second light paths that when projected onto the imaging station are approximately parallel but have opposite directions.

31. The system of claim 19 wherein the image management software prompts a user to take a specified sequence of at least five different images of body features of a subject.

32. The system of claim 31 wherein data from the five different images and a full facial image are combined in a subject profile.

33. The system of claim 1 wherein at least one light source has a light path that comprises an optical element to induce polarization.

34. The system of claim 22 wherein the light sources and the image sensor are part of an optics imaging attachment that is selectively connectable to and removable from the base unit.

35. A method for scoring a multidimensional body feature analysis for a subject, comprising using a processor to perform the steps of;

receiving a set of scores $N_i$ derived from image data and representing the condition of the subject's body feature as to three or more attributes (i);

defining for a set of three or more treatment products (p) and for each of the three or more attributes a set of scoring weights $W_{ip}$;

computing for each set of three or more treatment products a product-adjusted set of scores $AN_{ip}$, by applying the scoring weights $W_{ip}$ for each treatment product to the set of scores $N_i$ for the three or more attributes;

mapping each of the possible scores $N_i$ for each of the three or more attributes into a value on a rating scale ranging across at least three possible values $C_i$;

building a table for product recommendations, by associating with at least a plurality of the possible combinations of values on the rating scale a recommendation identifying one of the three or more treatment products; and mapping the scores $N_i$ of the subject into a set of values $\{C1, C2, C3 \ldots \}$ for the three or more attributes and finding the corresponding product recommendation in the table for product recommendations.

36. The method of claim 35 further comprising:

receiving from the subject a self-reporting response providing data relative to the subject's body feature; and responsive to the self-reporting response, adjusting at least one of the product-adjusted set of scores $AN_{ip}$.

37. The method of claim 35 further comprising:

receiving from the subject a self-reporting response providing data relative to the subject from at least two alternatives; and responsive to the self-reporting response, selecting a product recommendation without regard to any of the set of values $\{C1, C2, C3 \ldots \}$.

38. The method of claim 35, further comprising:

defining a self-reporting response providing data relative to the subject from at least two alternatives; and building into the table for product recommendations logic responsive to the alternatives in the self reporting response, whereby at least one of the two alternatives is logically associated with a product recommendation without regard to any of the set of values $\{C1, C2, C3 \ldots \}$.

39. The method of claim 35 wherein the body feature is skin and the three or more attributes of skin are three attributes selected from the group consisting of: discoloration, oil/shine, lines and wrinkles, texture and pores.

40. The method of claim 35 wherein the body feature is skin and the three or more attributes of skin are the following five attributes: discoloration, oil/shine, lines and wrinkles, texture and pores.

41. The method of claim 35 wherein the body feature is hair and the three or more attributes of hair are selected from the group consisting of: shine, cuticle size, angle of cuticle relative to hair shaft and hair shaft diameter.

42. A method for scoring a multidimensional body feature analysis for a subject, comprising using a processor to perform the steps of;

receiving a set of scores $N_i$ derived from image data and representing the condition of the subject's body feature as to three or more attributes (i);

defining for a set of three or more treatment products (p) and for each of the three or more attributes a set of scoring weights $W_{ip}$;

computing for each set of three or more treatment products a product-adjusted set of scores $AN_{ip}$, by applying the scoring weights Wip for each treatment product to the set of scores Ni for the three or more attributes;

receiving from the subject a self-reporting response providing data relative to the subject's body feature; and responsive to the self-reporting response, adjusting at least one of the product-adjusted set of scores ANip; wherein the self reporting response is a value on a scale ranging across at least three values; and the amount of adjustment to the at least one of the product-adjusted set of scores ANip is responsive to the differing values on the scale.

43. A method for scoring a multidimensional body feature analysis for a subject, comprising using a processor to perform the steps of;

receiving a set of scores Ni derived from image data and representing the condition of the subject's body feature as to three or more attributes (i);

defining for a set of three or more treatment products (p) and for each of the three or more attributes a set of scoring weights Wip; and computing for each set of three or more treatment products a product-adjusted set of scores ANip, by applying the scoring weights Wip for each treatment product to the set of scores Ni for the three or more attributes; wherein the scores ANip are product-adjusted normalized scores, the method further comprising:

responsive to the self-reporting response, making a treatment product selection; and responsive to the product selection response, reporting to the subject one product-adjusted normalized score ANip from the set of adjusted normalized scores ANip associated with the treatment product selection.

* * * * *